US010339653B2

(12) United States Patent
Gillies et al.

(10) Patent No.: US 10,339,653 B2
(45) Date of Patent: *Jul. 2, 2019

(54) SYSTEMS, METHODS AND DEVICES FOR ANALYZING QUANTITATIVE INFORMATION OBTAINED FROM RADIOLOGICAL IMAGES

(71) Applicants: H. Lee Moffitt Cancer Center and Research Institute, Inc., Tampa, FL (US); The Board of Trustees of the Leland Stanford Junior University, Palo Alto, CA (US); Stichting Maastricht Radiation Oncology 'Maastro Clinic', Maastricht (NL)

(72) Inventors: Robert J. Gillies, Tampa, FL (US); Steven A. Eschrich, Lakeland, FL (US); Robert A. Gatenby, Tampa, FL (US); Philippe Lambin, Bousval-Genappe (BE); Andreas L. A. J. Dekker, Maastricht (NL); Sandy A. Napel, Menlo Park, CA (US); Sylvia K. Plevritis, Los Altos Hills, CA (US); Daniel L. Rubin, Stanford, CA (US)

(73) Assignees: H. Lee Moffitt Cancer Center and Research Institute, Inc., Tampa, FL (US); The Board of Trustees of the Leland Stanford Junior University, Palo Alto, CA (US); Stichting Maastricht Radiation Oncology 'Maastro Clinic', Maastricht (NL)

( * ) Notice: Subject to any disclaimer, the term of this patent is extended or adjusted under 35 U.S.C. 154(b) by 0 days.

This patent is subject to a terminal disclaimer.

(21) Appl. No.: 15/664,530

(22) Filed: Jul. 31, 2017

(65) Prior Publication Data

US 2017/0358079 A1    Dec. 14, 2017

Related U.S. Application Data

(63) Continuation of application No. 14/912,150, filed as application No. PCT/US2014/050842 on Aug. 13, 2014, now Pat. No. 9,721,340.

(Continued)

(51) Int. Cl.
*A61B 6/00* (2006.01)
*A61B 5/00* (2006.01)
(Continued)

(52) U.S. Cl.
CPC .......... *G06T 7/0012* (2013.01); *A61B 5/055* (2013.01); *A61B 5/7271* (2013.01); *A61B 6/032* (2013.01);
(Continued)

(58) Field of Classification Search
CPC ............... G06T 7/00; G06K 9/00; A61B 5/00
(Continued)

(56) References Cited

U.S. PATENT DOCUMENTS

| 7,346,203 B2 | 3/2008 | Turek et al. |
| 7,783,094 B2 * | 8/2010 | Collins .................. A61B 6/00 382/128 |

(Continued)

FOREIGN PATENT DOCUMENTS

WO    2012/082789 A2    6/2012

OTHER PUBLICATIONS

International Search Report and Written Opinion of the International Searching Authority for Application No. PCT/US2014/050842, dated Nov. 19, 2014, 12 pages.
(Continued)

*Primary Examiner* — Abolfazl Tabatabai
(74) *Attorney, Agent, or Firm* — Meunier Carlin & Curfman LLC

(57) ABSTRACT

An example method for analyzing quantitative information obtained from radiological images includes identifying a ROI or a VOI in a radiological image, segmenting the ROI or the VOI from the radiological image and extracting quantitative features that describe the ROI or the VOI. The method also includes creating a radiological image record
(Continued)

including the quantitative features, imaging parameters of the radiological image and clinical parameters and storing the radiological image record in a data structure containing a plurality of radiological image records. In addition, the method includes receiving a request with the patient's radiological image or information related thereto, analyzing the data structure to determine a statistical relationship between the request and the radiological image records and generating a patient report with a diagnosis, a prognosis or a recommended treatment regimen for the patient's disease based on a result of analyzing the data structure.

24 Claims, 25 Drawing Sheets

Related U.S. Application Data

(60) Provisional application No. 61/865,544, filed on Aug. 13, 2013.

(51) Int. Cl.
*G06T 7/00* (2017.01)
*A61B 5/055* (2006.01)
*A61B 6/03* (2006.01)
*G06K 9/46* (2006.01)
*G06T 7/11* (2017.01)
*G06F 19/00* (2018.01)

(52) U.S. Cl.
CPC .............. *A61B 6/037* (2013.01); *A61B 6/463* (2013.01); *A61B 6/469* (2013.01); *A61B 6/5211* (2013.01); *A61B 6/5217* (2013.01); *G06K 9/46* (2013.01); *G06T 7/11* (2017.01); *G06F 19/321* (2013.01); *G06T 2207/10116* (2013.01); *G06T 2207/30096* (2013.01)

(58) Field of Classification Search
USPC .................................. 382/128–134; 600/300
See application file for complete search history.

(56) References Cited

U.S. PATENT DOCUMENTS 9,721,340 B2 * 8/2017 Gillies ................ A61B 5/7271
2013/0142412 A1   6/2013 Oh et al.

OTHER PUBLICATIONS

International Preliminary Report on Patentability issued in International Application No. PCT/US2014/050842, dated Feb. 25, 2016.
Notice of Allowance issued in U.S. Appl. No. 14/912,150, dated May 17, 2017.

* cited by examiner

SYSTEMS, METHODS AND DEVICES FOR ANALYZING QUANTITATIVE INFORMATION OBTAINED FROM RADIOLOGICAL IMAGES

CROSS REFERENCE TO RELATED APPLICATION

This application is a continuation application of U.S. application Ser. No. 14/912,150 filed Feb. 15, 2016, which will issue as U.S. Pat. No. 9,721,340 on Aug. 1, 2017, which is a 35 USC 371 application of international application PCT/US2014/050842 filed Aug. 13, 2014, which claims benefit of and priority to U.S. provisional patent application No. 61/865,544, entitled "Systems, Methods and Devices for Analyzing Quantitative Information Obtained from Radiological Images," filed on Aug. 13, 2013, all of which are hereby incorporated by reference in their entirety and made a part hereof.

STATEMENT REGARDING FEDERALLY FUNDED RESEARCH

This invention was made with Government support under Grant Nos. CA143062, CA160251 and CA142555 awarded by the National Institutes of Health. The Government has certain rights in the invention.

BACKGROUND

Current radiological practice is generally qualitative, e.g., in cancer care, "a peripherally enhancing spiculated mass in the lower left lobe." When radiological practice is quantitative, measurements are commonly limited to dimensional measurements of tumor size via one-dimensional (Response Evaluation Criteria In Solid Tumors [RECIST]) or two-dimensional (2D) (World Health Organization) long-axis measures. These quantitative measures do not reflect the complexity of tumor morphology or behavior, nor, in many cases, are changes in these measures predictive of therapeutic benefit. When additional quantitative measures are obtained, they generally average values over an entire region of interest (ROI).

Radiology is however moving towards more precise and more quantitative information extraction. Thus, radiological scans are moving from "imaging" modalities to "measurement" modalities, aided by tremendous increases in computational power and intelligent software. For example, algorithms exist to reliably segment regions of interest from radiological scans and extract quantitative descriptive features. There are also efforts to develop a standardized lexicon for describing lesions or tumors and to include these descriptors via annotated image markup into quantitative, mineable data. However, these approaches do not completely cover the range of quantitative features that can be extracted from images, such as texture, shape or margin gradients.

SUMMARY

An example method for analyzing quantitative information obtained from radiological images can include identifying a region of interest (ROI) or a volume of interest (VOI) in a radiological image, segmenting the ROI or the VOI from the radiological image and extracting a plurality of quantitative features that describe the ROI or the VOI from the radiological image. Herein, ROI or VOI may include a tumor region and/or its the surroundings. it may also be other organ systems, non cancerous. The method can also include creating a radiological image record including the quantitative features describing the ROI or the VOI from the radiological image, imaging parameters related to the radiological image and clinical parameters and storing the radiological image record in a data structure containing a plurality of radiological image records. In addition, the method can include receiving a request related to a patient's radiological image, where the request includes the patient's radiological image or information related to a patient's radiological image, analyzing the data structure to determine a statistical relationship between the request and the plurality of radiological image records and generating a patient report (e.g., a patient decision support report) with a diagnosis, a prognosis or a recommended treatment regimen for the patient's disease based on a result of analyzing the data structure. The statistical or numerical relationship between the request and plurality of radiological image records can be either determined at the time of the request or pre-determined and be embodied in a mathematical equation that is applied. In addition, the method can be used to develop, in a stand-alone platform, relationships between the image features and patient characteristics, including clinical responses to therapy or prognostic information Optionally, five or more quantitative features that describe the ROI or the VOI from the radiological image are extracted. Alternatively or additionally, approximately one thousand quantitative features that describe the ROI or the VOI from the radiological image are optionally extracted. Alternatively or additionally, approximately two thousand quantitative features that describe the ROI or the VOI from the radiological image are optionally extracted.

In addition, the quantitative features that describe the ROI or the VOI in the radiological image can include a shape-based feature, a texture-based feature or a habitat feature. Alternatively, the quantitative features can optionally include a shape-based feature, a texture-based feature and a habitat feature. Additionally, the quantitative features can optionally include an intensity feature and/or a position-based feature.

Optionally, the imaging parameters related to the radiological image can include resolution parameter(s), reconstruction parameter(s) and acquisition parameter(s). For example, the imaging parameters can be included in a DICOM header of the radiological image.

Optionally, the clinical parameters can include a disease type, a disease stage, a treatment history and a clinical outcome. The treatment history can be a treatment regimen, for example, a prescribed drug, a clinical trial or a medical procedure. Optionally, the treatment history can include information about the prescribed drug including at least one of a name, a strength or a number of refills of the prescribed drug. Alternatively or additionally, the treatment history can optionally include information about a change in a disease and a treatment regimen prescribed in response to the change in the disease. For example, the change in the disease can be a relapse of the disease or a healing of the disease. Alternatively or additionally, the clinical outcome can be a response to therapy, a time to progression, a progression-free survival, a disease-free survival or an overall survival. Alternatively or additionally, the clinical outcome can optionally include an objective assessment of response to therapy or a subjective assessment of response to therapy.

Optionally, the radiological image record can include molecular, genetic, genomic or proteomic data. Alternatively or additionally, the radiological image record can optionally include demographic data and/or risk factor data. Alternatively or additionally, the radiological image record can include tissue data.

Optionally, analyzing the data structure to determine a statistical relationship between the request and the plurality of radiological image records can include using a pattern recognition technique to identify patterns relevant to the patient's disease that are present in the data structure. For example, the pattern recognition technique can be a distance matching algorithm.

Optionally, the method can include transmitting the patient report in response to the request. Alternatively or additionally, the patient report can optionally include a probability for the diagnosis, the prognosis or the recommended treatment regimen for the patient's disease. Optionally, the patient report can include a reliability coefficient associated with the probability for the diagnosis, the prognosis or the recommended treatment regimen for the patient's disease.

In some implementations, the request related to the patient's radiological image includes the patient' radiological image. In these implementations, the method can further include identifying a ROI or a VOI in the patient's radiological image, segmenting the ROI or the VOI from the patient's radiological image and extracting a plurality of quantitative features that describe the ROI or the VOI from the patient's radiological image. The information related to the patient's radiological image can be the plurality of quantitative features that describe the ROI or the VOI from the patient's radiological image and one or more imaging parameters related to the patient's radiological image. Optionally, the data structure can be analyzed to determine a statistical relationship between the information related to the patient's radiological image and the plurality of radiological image records.

In other implementations, the request related to the patient's radiological image can be the information related to the patient's radiological image, which can be the plurality of quantitative features that describe the ROI or the VOI from the patient's radiological image and one or more imaging parameters related to the patient's radiological image. Optionally, the data structure can be analyzed to determine a statistical relationship between the information related to the patient's radiological image and the plurality of radiological image records.

Optionally, the information related to the patient's radiological image can include the patient's molecular, genetic, genomic or proteomic data or the patient's demographic data and/or risk factor data. Alternatively or additionally, the radiological image record can include the patient's tissue data.

Alternatively or additionally, the method can optionally include receiving the radiological image from one of a plurality of archives, where each of the archives comprising a plurality of radiological images.

Alternatively or additionally, extracting a plurality of quantitative features that describe the ROI or the VOI in the radiological image can optionally include extracting a plurality of quantitative features that describe an area at least partially surrounding the ROI or the VOI in the radiological image.

Alternatively or additionally, the ROI or the VOI in the radiological image can optionally be segmented from the radiological image using segmentation algorithms, for example a region-growing algorithm, a level set algorithm, a graph cut algorithm, an active contour algorithm or a livewire algorithm.

Optionally, the method can include storing the radiological image in the data structure. Alternatively or additionally, the method can optionally include stripping confidential patient information from the radiological image and assigning the radiological image a de-identified number. The radiological image record can optionally include the de-identified number.

Alternatively or additionally, each of the plurality of radiological image records stored in the data structure can include a plurality of quantitative features that describe a ROI or a VOI in each respective radiological image, imaging parameters related to each respective radiological image and clinical parameters.

Optionally, the radiological image can be obtained by computed tomography (CT), magnetic resonance imaging (MRI) or positron emission tomography (PET).

Another example method for analyzing quantitative information obtained from radiological images can include identifying a ROI or a VOI in a patient's radiological image, segmenting the ROI or the VOI from the patient's radiological image and extracting a plurality of quantitative features that describe the ROI or the VOI from the patient's radiological image. The method can also include transmitting a request with the plurality of quantitative features that describe the ROI or the VOI from the patient's radiological image and imaging parameters related to the patient's radiological image and receiving a patient report (e.g., a patient decision support report) in response to the request. The patient report can include a diagnosis, a prognosis or a recommended treatment regimen for the patient's disease. The patient report can be obtained by analyzing a data structure containing a plurality of radiological image records to determine a statistical relationship between the request and the plurality of radiological image records. Each of the plurality of radiological image records stored in the data structure can include a plurality of quantitative features that describe a ROI or a VOI in each respective radiological image, imaging parameters related to each respective radiological image and clinical parameters.

Optionally, the request can further include the patient's molecular, genetic, genomic or proteomic data or the patient's demographic data and/or risk factor data. Alternatively or additionally, the radiological image record can include tissue data.

Optionally, five or more quantitative features that describe the ROI or the VOI from the patient's radiological image are extracted. Alternatively or additionally, approximately one thousand quantitative features that describe the ROI or the VOI from the patient's radiological image are optionally extracted. Alternatively or additionally, approximately two thousand quantitative features that describe the ROI or the VOI from the patient's radiological image are optionally extracted.

In addition, the quantitative features that describe the ROI or the VOI in the patient's radiological image can include a shape-based feature, a texture-based feature or a habitat feature. Alternatively, the quantitative features can optionally include a shape-based feature, a texture-based feature and a habitat feature. Additionally, the quantitative features can optionally include an intensity feature or a position-based feature.

Optionally, the imaging parameters related to the radiological image can include resolution parameter(s), reconstruction parameter(s) and acquisition parameter(s). For example, the imaging parameters can be included in a DICOM header of the radiological image.

Optionally, the clinical parameters can include a disease type, a disease stage, a treatment history and a clinical outcome. The treatment history can be a treatment regimen, for example, a prescribed drug, a clinical trial or a medical procedure. Optionally, the treatment history can include information about the prescribed drug including at least one of a name, a strength or a number of refills of the prescribed drug. Alternatively or additionally, the treatment history can optionally include information about a change in a disease and a treatment regimen prescribed in response to the change in the disease. For example, the change in the disease can be a relapse of the disease or a healing of the disease. Alternatively or additionally, the clinical outcome can be a response to therapy, a time to progression, a progression-free survival, a disease-free survival or an overall survival. Alternatively or additionally, the clinical outcome can optionally include an objective assessment of response to therapy or a subjective assessment of response to therapy.

Optionally, the patient report can optionally include a probability for the diagnosis, the prognosis or the recommended treatment regimen for the patient's disease. Optionally, the patient report can include a reliability coefficient associated with the probability for the diagnosis, the prognosis or the recommended treatment regimen for the patient's disease.

Optionally, analyzing the data structure to determine a statistical relationship between the request and the plurality of radiological image records can include using a pattern recognition technique to identify patterns relevant to the patient's disease that are present in the data structure. For example, the pattern recognition technique can be a distance matching algorithm.

Alternatively or additionally, extracting a plurality of quantitative features that describe the ROI or the VOI in the patient's radiological image can optionally include extracting a plurality of quantitative features that describe an area or volume at least partially surrounding the ROI or the VOI in the patient's radiological image.

Alternatively or additionally, the ROI or the VOI in the radiological image can optionally be segmented from the radiological image using the assistance of segmentation algorithms in whole or in-part, for example a region-growing algorithm, a level set algorithm, a graph cut algorithm, an active contour algorithm or a livewire algorithm.

Optionally, the patient's radiological image can be obtained by CT, MRI or PET.

It should be understood that the above-described subject matter may also be implemented as a computer-controlled apparatus, a computer process, a computing system, or an article of manufacture, such as a computer-readable storage medium.

Other systems, methods, features and/or advantages will be or may become apparent to one with skill in the art upon examination of the following drawings and detailed description. It is intended that all such additional systems, methods, features and/or advantages be included within this description and be protected by the accompanying claims.

BRIEF DESCRIPTION OF THE DRAWINGS

The components in the drawings are not necessarily to scale relative to each other. Like reference numerals designate corresponding parts throughout the several views.

DETAILED DESCRIPTION

Unless defined otherwise, all technical and scientific terms used herein have the same meaning as commonly understood by one of ordinary skill in the art. Methods and materials similar or equivalent to those described herein can be used in the practice or testing of the present disclosure. As used in the specification, and in the appended claims, the singular forms "a," "an," "the" include plural referents unless the context clearly dictates otherwise. The term "comprising" and variations thereof as used herein is used synonymously with the term "including" and variations thereof and are open, non-limiting terms. The terms "optional" or "optionally" used herein mean that the subsequently described feature, event or circumstance may or may not occur, and that the description includes instances where said feature, event or circumstance occurs and instances where it does not. While implementations will be described for analyzing quantitative information obtained from radiological images of a patient with cancer, it will become evident to those skilled in the art that the implementations are not limited thereto, but are applicable for analyzing quantitative information obtained from radiological images of a patient with other diseases such as, inter alia, cardiovascular disease, autoimmune disease, trauma, neurodegenerative or psychiatric disorders, or infectious diseases. It should also be understood that the implementations are also applicable for analyzing quantitative information obtained from radiological images of a patient with no diseases such as in a screening setting, for example.

Figure 1:
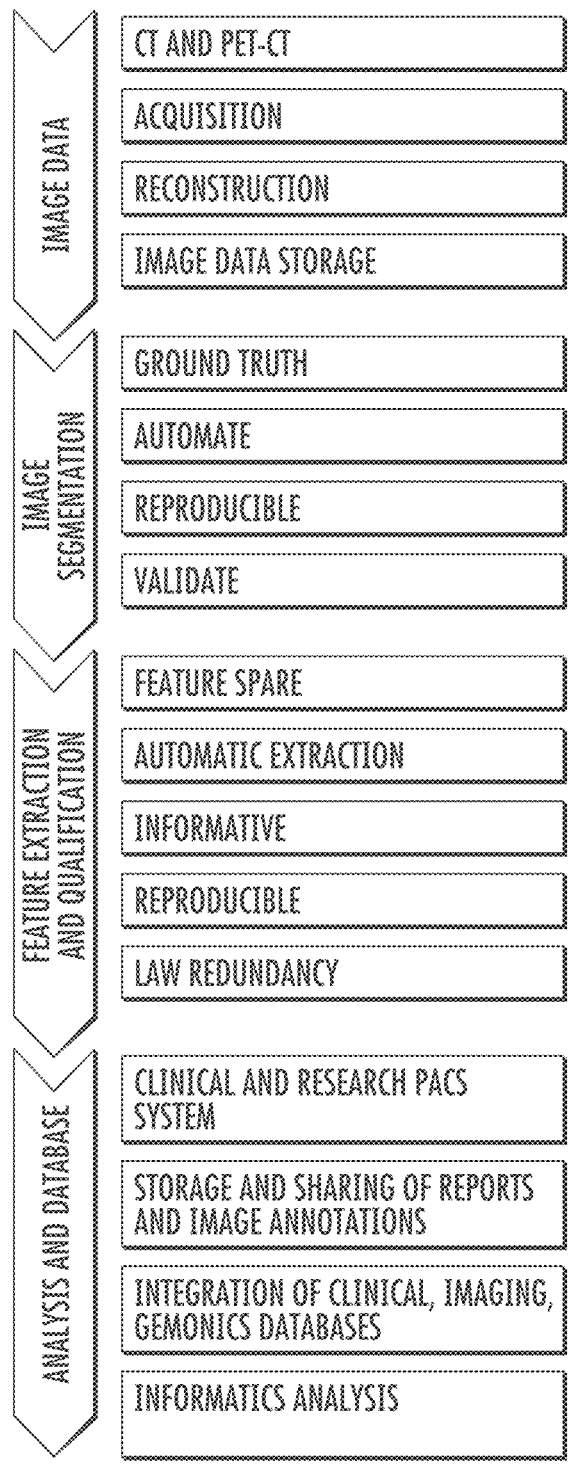
FIG. 1 is a chart illustrating the processes and challenges of radiomics.

"Radiomics" involves the high-throughput extraction of quantitative imaging features with the intent of creating mineable databases from radiological images. Such analyses and mining of image feature data can reveal quantitative predictive or prognostic associations between images and medical outcomes. The goal of radiomics is to convert images into mineable data, with high fidelity and high throughput. The radiomics enterprise can be divided into five processes with definable inputs and outputs, each with its own challenges that need to be overcome: (a) image acquisition and reconstruction, (b) image segmentation and rendering, (c) feature extraction and feature qualification, (d) databases and data sharing and (e) ad hoc informatics analyses. FIG. 1 is a chart illustrating the processes and challenges of radiomics. Each of these steps must be developed de novo and, as such, poses discrete challenges. For example, protocols for image acquisition and reconstruction have to be identified and harmonized. Segmentations have to be robust and involve minimal operator input. Features have to be generated that robustly reflect the complexity of the individual volumes, but cannot be overly complex or redundant. Informatics databases that allow for incorporation of image features and image annotations, along with medical and genetic data, have to be generated. Finally, the statistical approaches to analyze these data have to be optimized. Additionally, because variation in results may come from variations in any of these individual processes, another level of challenge is to harmonize and standardize the entire process, while still allowing for improvement and process evolution.

It should be appreciated that the logical operations described herein with respect to the various figures are implemented (1) as a sequence of computer implemented acts or program modules running on a computing system and/or (2) as interconnected machine logic circuits or circuit modules within the computing system. The implementation is a matter of choice dependent on the performance and other requirements of the computing system. Accordingly, the logical operations described herein are referred to variously as operations, structural devices, acts, or modules. These operations, structural devices, acts and modules may be implemented in software, in firmware, in special purpose digital logic, and any combination thereof. It should also be appreciated that more or fewer operations may be performed than shown in the figures and described herein. These operations may also be performed in a different order than those described herein.

Figure 2A:
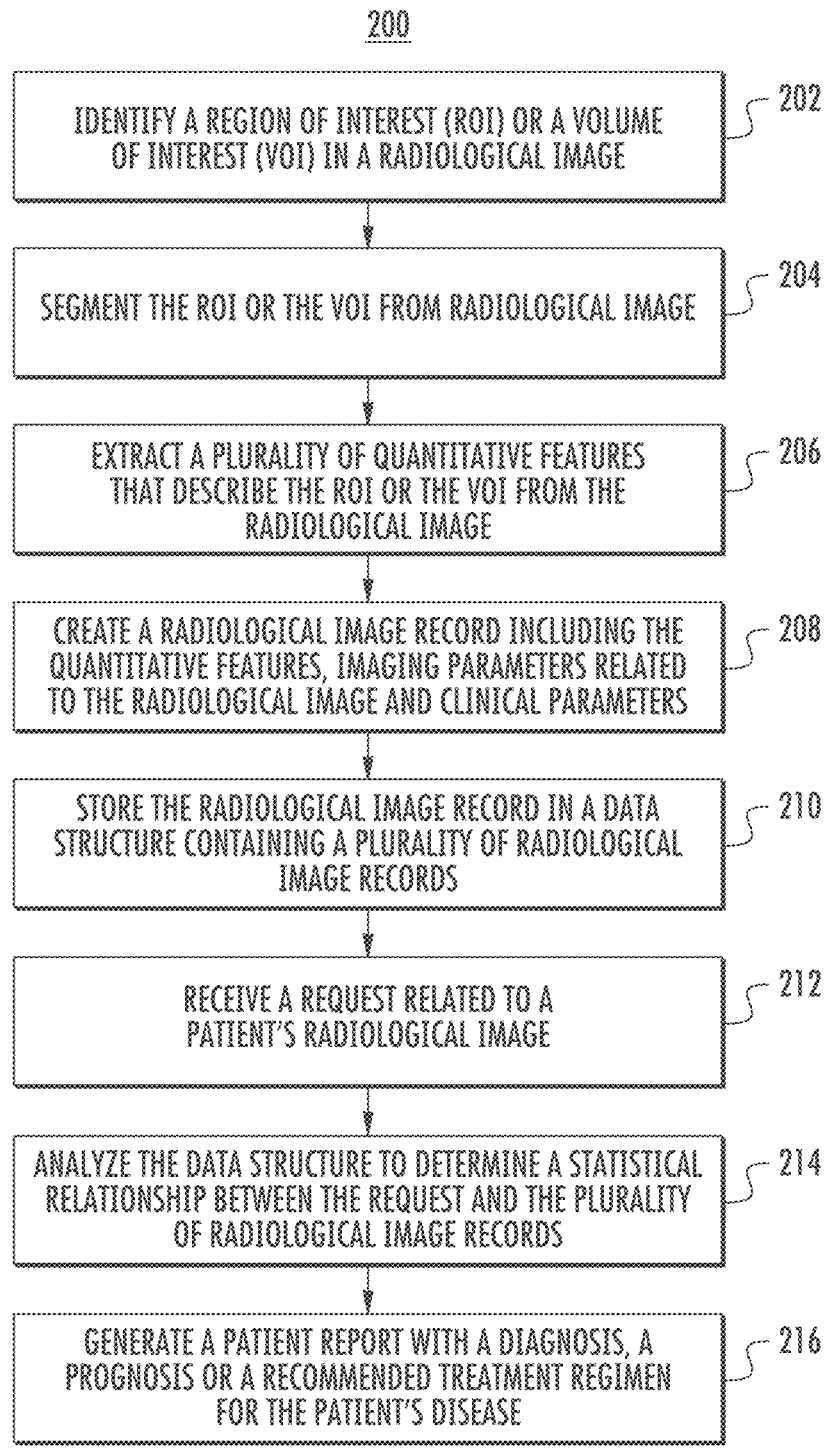
FIGS. 2A-2B are flow charts illustrating example operations for analyzing quantitative information obtained from radiological images.

Referring now to FIG. 2A, a flow chart illustrating example operations 200 for analyzing quantitative information obtained from radiological images is shown. This disclosure contemplates that the example operations 200 can optionally be performed by a "content provider," which can be one or more academic, hospital or community-based radiology practices committed to providing high-quality radiographic images along with patient data which may include, inter alia, patient demographics, therapeutic interventions, responses to therapeutic interventions, and/or other relevant medical data and outcomes. This disclosure contemplates that the content provider can use one or more computing devices (e.g., the computing device described with regard to FIG. 10) to perform the example operations. At 202, a region of interest (ROI) or a volume of interest (VOI) in a radiological image can be identified. Techniques for identifying ROIs or VOIs in radiological images are known in the art. This disclosure contemplates using any known technique for indentifying the ROI or the VOI. In addition, the radiological image can be obtained from one of a plurality of image repositories or archives such as the National Biomedical Image Archive (NBIA) hosted by the National Cancer Institute (The Cancer Imaging Archive, or TCIA), for example. Although TCIA is provided as an example, this disclosure contemplates that other image repositories or sources can be used including the Picture Archiving and Communications Systems (PACS) of one or more entities that store clinical radiological images. Additionally, the radiological image can be an image obtained by techniques or modalities including computed tomography (CT), magnetic resonance imaging (MRI) and positron emission tomography (PET). These imaging techniques are provided only as examples. Thus, this disclosure contemplates that other imaging techniques can be used.

At 204, the ROI or the VOI can be segmented from the radiological image. The ROI or the VOI in the radiological image can include an organ, a cancerous tumor, and/or the region at least partially surrounding the organ or cancerous tumor. The ROI or VOI can optionally be segmented from the radiological image using segmentation algorithms with or without user input (e.g., semi-automated or fully automated segmentation algorithms). Segmentation algorithms can include, inter alia, one of a region-growing algorithm, a level set algorithm, a graph cut algorithm, an active contour algorithm and a livewire algorithm. It should be understood that these techniques are provided only as examples and that other known segmenting techniques can be used. After segmenting the ROI or the VOI from the radiological image, a plurality of quantitative features that describe the ROI or the VOI from the radiological image can be extracted at 206. Optionally, a plurality of quantitative features that describe an area at least partially surrounding the ROI or the VOI (e.g., in tissue surrounding a lesion or tumor) in the radiological image can be extracted. Optionally, five or more quantitative features can be extracted. Alternatively or additionally, approximately one hundred, five hundred, one thousand or two thousand quantitative features can optionally be extracted. The numbers of extracted quantitative features described above are provided only as example and this disclosure contemplates extracting more or less quantitative features than provided herein.

The quantitative features can include one or more shape-based features, texture-based features or habitat features. Shape-based features include features describing the location, geometric shape, volume, surface area and/or surface-area-to-volume ratio of a lesion or tumor. Shape-based features can also include descriptors of tumor compactness and/or shape (e.g., sphericity). Texture-based features can include features describing autocorrelation, contrast, correlation, cluster prominence, cluster shade, cluster tendency, dissimilarity, energy, homogeneity, maximum probability, sum of squares, sum average, sum variance, sum entropy and/or difference entropy of a lesion or tumor. Habitat features are shape and texture features that are extracted from sub-regions within tumors that are delineated by specific algorithms applied to single or multiple imaging tests. Habitat features can describe radiologically-defined regional variations within a tumor or lesion. Further, habitat features can be features extracted from regions bordering, adjacent or distal from the tumor. It should be understood that the examples of shape-based, texture-based and habitat features are provided only as examples and that other shape-based, texture-based and habitat features can be extracted. In some implementations, the quantitative features can optionally include at least one of each of shape-based features, texture-based features and habitat features. This disclosure contemplates that other types of quantitative features can optionally be extracted, including, but not limited to, intensity features or position-based features.

At 208, a radiological image record can be created, which includes the quantitative features describing the ROI or the VOI from the radiological image, imaging parameters related to the radiological image and clinical parameters. The imaging parameters related to the radiological image can include a resolution parameter, a reconstruction parameter and an acquisition parameter. For example, the imaging parameters can be included in the radiological image metadata such as a DICOM header, for example. Additionally, the clinical parameters can include a disease type, a disease stage, a treatment history and a clinical outcome. Optionally, the radiological image record can include molecular, genetic, genomic, proteomics or tissue data in addition to the disease type, the disease stage, the treatment history and the clinical outcome. Alternatively or additionally, the radiological image record can optionally include demographic data in addition to the disease type, the disease stage, the treatment history and the clinical outcome.

The treatment history can be a treatment regimen, for example, a prescribed drug, a clinical trial or a medical procedure. Optionally, the treatment history can include information about the prescribed drug including a name, a strength and/or a number of refills of the prescribed drug. The treatment history can also optionally include information about a change in a disease and a treatment regimen prescribed in response to the change in the disease (e.g., a response biomarker). For example, the change in the disease can be a relapse of the disease or a healing of the disease. The clinical outcome can be a response to therapy, a time to progression, a progression-free survival, a disease-free survival or an overall survival. Alternatively or additionally, the clinical outcome can optionally include an objective assessment of response to therapy or a subjective assessment of response to therapy. Additionally, the molecular, genetic, genomic or proteomic data can include, inter alia, gene expression profiling, single nucleotide polymorphisms, exome sequencing, whole genome sequencing, etc. It should be understood that the genetic or genomic data should not be limited to the examples provided above. Additionally, tissue data can include digitized histopathology images, quantitative features extracted from the histopathology images, immunohistochemistry (IHC) images, and quantitative features extracted from IHC images. For example, biopsies are commonly acquired from cancer patents and the subsequent histology exams are used to provide definitive diagnoses. In many cases, these slides are scanned and stored in digital format. These digital images and the pathodiagnosis can be included in the radiological image record. Additionally, these digital images can optionally be analyzed by feature extraction routines, and these extracted features can be used in a likewise fashion. Additionally, IHC can be used to examine the expression and distribution of specific proteins in a pathology sample. This information can also be included in the genomic report (as it is considered proteomics), as well as the digitized and quantitatively analyzed images. Additionally, the demographic data concerning the patient can include, inter alia, a gender of the patient, a marital status of the patient, an ethnicity of the patient, a primary language spoken by the patient, the color of the eyes of the patient, the hair color of the patient, the height of the patient, the weight of the patient, the social security number of the patient, the name of the patient, the date of birth of the patient, the educational status of the patient, an identity of the primary physician for the patient, a name of a referring physician for the patient, a referral source for the patient, an indication as to whether the patient is disabled and a description of the disability, an indication as to whether the patient is a smoker, an indication as to whether the patient consumes alcohol, a residential address of the patient, a telephone number of the patient, a name of an insurance carrier for an insurance policy held by the patient and/or a member identifier number for an insurance policy held by the patient.

At 210, the radiological image record can be stored in one or more data structures (e.g., a database) containing a plurality of radiological image records. This disclosure contemplates that the data structure can contain a large number of radiological image records. For example, the data structure can optionally contain in excess of one hundred thousand radiological image records. As discussed above, the radiological image records can be obtained by analyzing (e.g., identifying an ROI/VOI, segmenting the ROI/VOI and extracting a plurality of quantitative features) radiological images stored in more than one image archive. In other words, a large number of radiological images can be obtained from a plurality of sources, and each of the radiological images can be processed as described in steps 202-210. This disclosure contemplates that each of the plurality of radiological image records stored in the data structure can include a plurality of quantitative features that describe a ROI or a VOI in each respective radiological image, imaging parameters related to each respective radiological image and clinical parameters. Additionally, each of the plurality of radiological image records stored in the data structure can optionally include genetic or genomic data, tissue data and/or demographic data as discussed above. Optionally, the radiological image can also be stored in the data structure (e.g., in addition to the radiological image record) or in another data structure. In some implementations, confidential information (e.g., confidential patient information) can be stripped from the radiological image, and a de-identified number can be assigned. The radiological image record can optionally include the de-identified number, for example, instead of including confidential information.

In some implementations, the radiological image records (e.g., the file containing the quantitative features, etc.) can optionally be stored in a central repository (e.g., one or more data structures or databases) of a central server system. Optionally, the radiological images (e.g., the actual image data set, the raw unprocessed (time domain) data, etc.) can also be stored in the central repository. In this case, the radiological images can optionally be linked to their respective radiological image records. Alternatively, the radiological images can be maintained separately from the radiological image records stored in the central repository. For example, the radiological images can be stored locally at the one or more content providers, e.g., remote from the central server system. When the radiological image records are stored in the central repository, a decision support system (DSS) module, for example a module executing on the central server system, can query and analyze the plurality of radiological image records as described in detail below. This disclosure contemplates that the DSS module can be configured to receive the patient request related to the patient's radiological image record (e.g., step 212), analyze the data structure (e.g., step 214) and/or generate the patient report (e.g., step 216). Additionally, the DSS module can optionally be configured to perform steps 202-210 described above.

In other implementations, the radiological image records, and optionally the radiological images, can be stored locally at the one or more content providers (e.g., at one or more federated repositories). When the radiological image records are stored locally at one or more federated repositories, the DSS module, for example a module executing on the central server system, can query and analyze the plurality of radiological image records as described in detail below. In other words, the DSS module can be configured to access the radiological image records stored one locally at one or more federated repositories. This disclosure contemplates that the DSS module can be configured to receive the patient request related to the patient's radiological image record (e.g., step 212), analyze the data structure (e.g., step 214) and/or generate the patient report (e.g., step 216).

At 212, a request related to a patient's radiological image can be received at a centralized or local instance of the software. The request may be at any time after the process performed at 210 and may be received independently of the performance of 202-210. For example, an end user (discussed below) can send a request directly or indirectly to the central server system that supports the DSS module described above. The request can include the patient's radiological image or information related to a patient's radiological image. In some implementations, the request includes the patient's radiological image, and the content provider can process the patient's radiological image. For example, the content provider can perform the following processes: identifying a ROI or a VOI in a patient's radiological image, segmenting the ROI or the VOI from the patient's radiological image and extracting a plurality of quantitative features that describe the ROI or the VOI from the patient's radiological image. These processes are similar to steps 202-206 (except that they are performed on the patient's radiological image received in the request instead of on the radiological image obtained from one of a plurality of image repositories) and are therefore not described in further detail below. In these implementations, the plurality of quantitative features that describe the ROI or the VOI from the patient's radiological image and one or more imaging parameters related to the patient's radiological image become the "information related to the patient's radiological image" as used herein. Optionally, the information related to the patient's radiological image can also include the patient's genetic or genomic data, tissue data or the patient's demographic data. In other implementations, the end user processes the patient's radiological image (described with regard to FIG. 2B), and the end user sends the request including information related to the patient's radiological image (e.g., the plurality of quantitative features that describe the ROI or the VOI from the patient's radiological image and one or more imaging parameters related to the patient's radiological image) to the content provider. Similar to above, the information related to the patient's radiological image can also optionally include the patient's genetic or genomic data or the patient's demographic data.

At 214, the data structure can be analyzed to determine a statistical relationship between the request and the plurality of radiological image records. For example, the data structure can be analyzed to determine a statistical relationship between the information related to the patient's radiological image and the plurality of radiological image records. In other words, the data structure can be analyzed to identify patterns present in the radiological image records (e.g., including quantitative features, imaging parameters and clinical parameters) that are relevant to the information contained in the patient's radiological image (e.g., quantitative features and imaging parameters). For example, the data structure can be analyzed to identify statistical relationships between the quantitative features (and/or genomic features) present in the radiological image records and the patient's request and clinical outcomes. These analyses make use of classifier models to precisely identify relationships between the patient's request and the plurality of radiological image records stored in the central or federated repositories. This analysis can then be used for decision support by providing general or specific treatment recommendations, for prognosis and prediction, respectively. The statistical relationships (e.g., models) can optionally generate probabilities with or without reliability coefficients for distinct events based on the input data (e.g., the patient's request). By identifying patterns present in the radiological image records, it is possible provide a diagnosis, a prognosis and/or a recommended therapy (e.g., a drug regimen, a clinical trial, a medical procedure, etc.). This disclosure contemplates using a pattern recognition technique to identify patterns relevant to the patient's disease that are present in the data structure. The pattern recognition technique can be used to build one or more classifier models, which can be used by the DSS module, for example, to provide treatment recommendation (e.g., the patient report described in detail below). A number of pattern recognition techniques are known in the art. For example, the pattern recognition technique can be a distance matching algorithm. Example distance matching algorithms include, but are not limited to, k nearest neighbors or a model-based technique such as logistic regression or support vector machines.

At 216, a patient report can be generated with a diagnosis, a prognosis or a recommended treatment regimen for the patient's disease based on a result of analyzing the data structure. The patient report can optionally include a probability for the diagnosis, the prognosis or the recommended treatment regimen for the patient's disease. In addition, the patient report can optionally include a reliability coefficient associated with the probability for the diagnosis, the prognosis or the recommended treatment regimen for the patient's disease. Optionally, the patient report can be transmitted in response to the request, e.g., from the content provider to the end user.

Figure 2B:
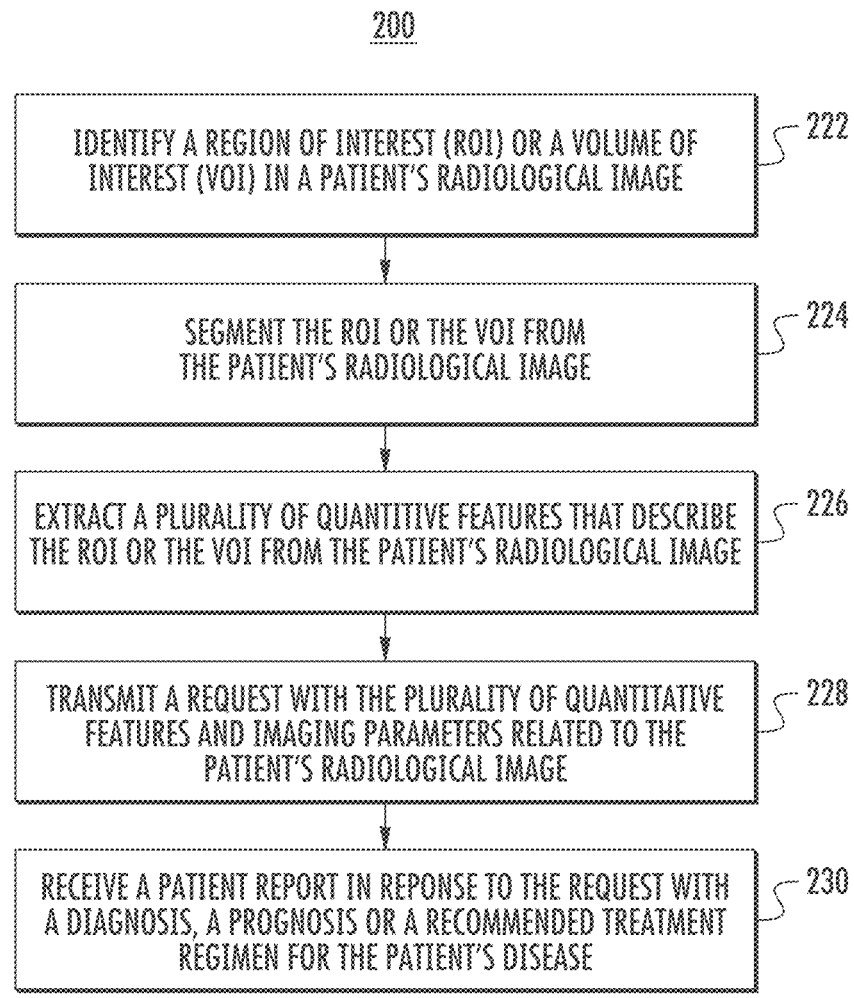

Referring now to FIG. 2B, a flow chart illustrating example operations 220 for analyzing quantitative information obtained from radiological images is shown. This disclosure contemplates that the example operations 220 can optionally be performed by an "end user," which can be a patient, a treating physician, a radiologist, a hospital, a cancer care center, an insurance company or any other medical professional using one or more computing devices (e.g., the computing device described with regard to FIG. 10). At 222, a ROI or a VOI can be identified in a patient's radiological image. At 224, the ROI or the VOI can be segmented from the patient's radiological image. At 226, a plurality of quantitative features that describe the ROI or the VOI from the patient's radiological image can be extracted. Steps 222-226 are similar to steps 202-206 in FIG. 2A and are therefore not described in detail below. In other words, in accordance with steps 222-226, the end user processes the patient's radiological image to obtain the quantitative features. Then, at 228, a request with the plurality of quantitative features that describe the ROI or the VOI from the patient's radiological image can be transmitted. The request can also include the imaging parameters related to the patient's radiological image. Optionally, the request can also include the patient's genetic or genomic data, tissue data and/or the patient's demographic data. It should be understood that the request can be transmitted from the end user to the content provider. At 230, a patient report can be received in response to the request. Similar to FIG. 2A, the patient report can include a diagnosis, a prognosis or a recommended treatment regimen for the patient's disease.

The patient report can be obtained by analyzing a data structure containing a plurality of radiological image records to determine a statistical relationship between the request and the plurality of radiological image records. These processes are described in detail with regard to FIG. 2A (e.g., steps 214-216) and are therefore not described in further detail below.

Figure 3:
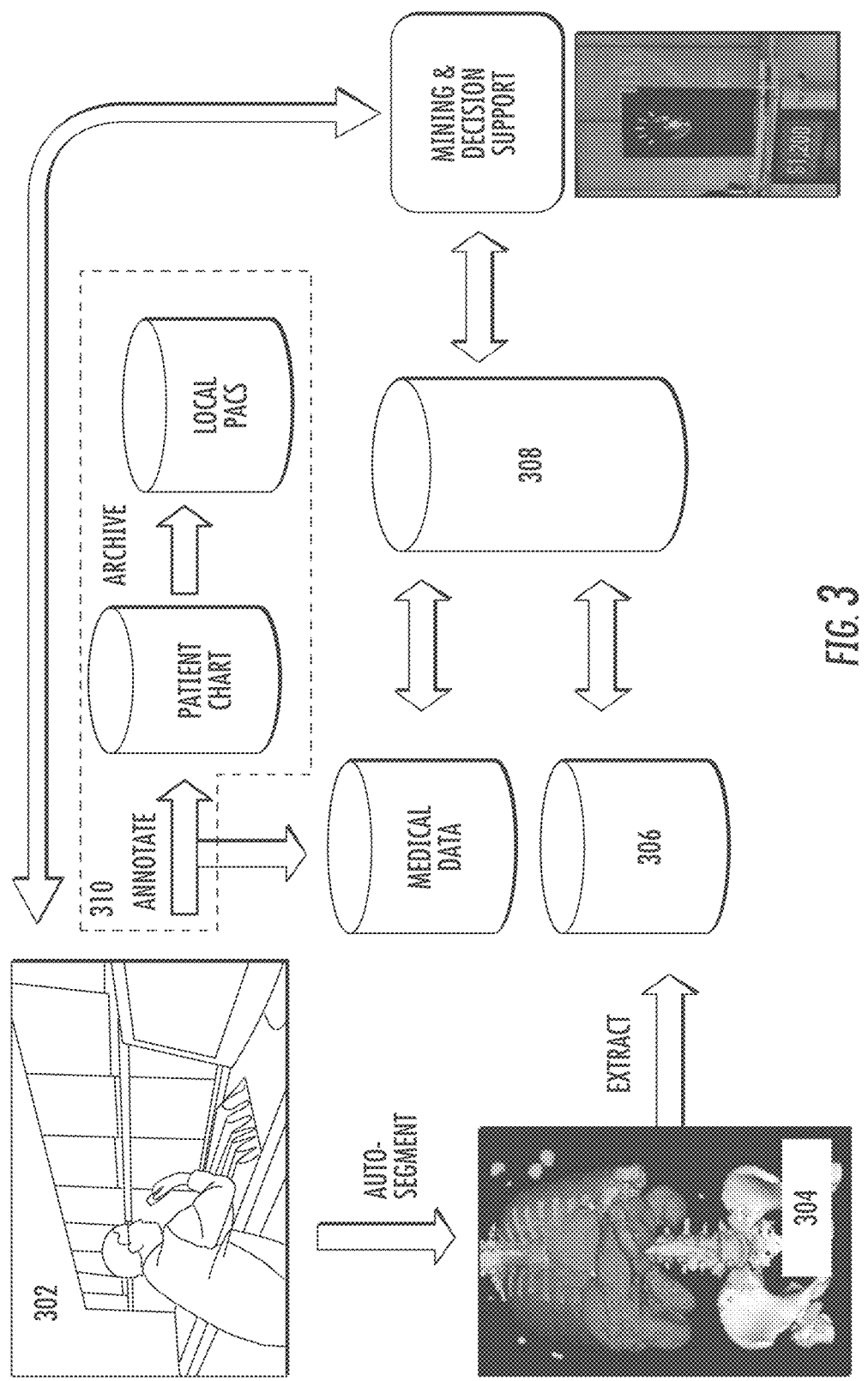
FIG. 3 is another flow chart illustrating example operations for analyzing quantitative information obtained from radiological images.

Referring now to FIG. 3, another flow chart illustrating example operations for analyzing quantitative information obtained from radiological images is shown. In FIG. 3, the examples operations for analyzing quantitative information according to techniques described herein are shown with reference to conventional processes. Conventionally, an end user 302 annotates a radiological image, which is then stored in a patient's chart and/or a local PACS. This is shown by dotted line 310. According to the techniques described herein, a content provider can create and/or maintain a data structure 306 for storing a plurality of radiological image records. As described above, the content provider can analyze a plurality of radiological images from one or more image repositories 308 (e.g., NBIA) and create the radiological image records for storing in the data structure 306. These processes are described in detail with regard to FIG. 2A and are therefore not described in detail below. As shown in FIG. 3, the end user can analyze a patient's radiological image 304, for example, by identifying a ROI/VOI, segmenting the ROI/VOI and extracting a plurality of quantitative features, processes which are described in detail with regard to FIG. 2B. The data structure 306 can then be analyzed (e.g., mined) to provide a diagnosis, a prognosis and/or a recommended treatment regimen. As described above, this information can be provided to the end user by the content provider and/or the decision support module.

Optionally or additionally, the processes above may be used in the analysis of images generated using low-dose CT screening for lung cancer that is used in certain high-risk populations. In such screenings, there is an over-classification of patients as having cancer than actually have it. Low-dose CT images can be analyzed using the radiomics methods above to improve the accuracy of the diagnosis of lung cancer. For example, a combination of features or subset of features may be used that strongly correlate to the presence or absence of cancerous tumors.

EXAMPLES

The above description provides operational flows for obtaining and analyzing quantitative information from radiological images. Below are specific, non-limiting, examples of systems and processes that may be used in one or more of the operational flows above.

Image Acquisition and Reconstruction

In routine clinical image acquisition, there is wide variation in imaging parameters such as image resolution (e.g., pixel size or matrix size and slice thickness), washout period in the case of PET imaging, patient position, and the variations introduced by different reconstruction algorithms and slice thicknesses, which are different for each scanner vendor. Imaging issues can create difficulty in comparing results obtained across institutions with different scanners and patient populations. In addition, it is a challenge to identify and curate a large number of image data examples with similar clinical parameters such as disease stage.

CT Imaging

Figure 4:
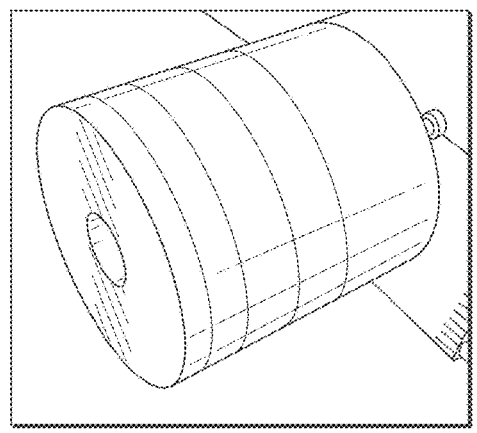
FIG. 4 is an example CT phantom.

Of all the imaging modalities, CT appears to be the most straightforward and perhaps the easiest to compare across institutions and vendors. Standard phantoms such as the CT phantom shown in FIG. 4 have become the standard of the industry. This phantom has several regions to test image quality such as low contrast detectability and spatial resolution. The phantom is based on the American Association of Physicists in edicine (Task Group Report-1) and has several sections to evaluate imaging performance. There are sections (a) to evaluate the true slice thickness and variation of Hounsfield units (HUs) with electron density, (b) to look at the ability to visualize small variations in density (low contract delectability) and another (c) for detecting special resolution, high contrast detectability, and a region of uniform medium to examine variation in HUs. The imaging performance of a scanner will depend also on the imaging technique. As the slice thickness is reduced, the photon statistics within a slice are reduced unless the mA or kVp is increased. The axial field of view will also change the voxel size within a slice, and the reconstruction matrix size can also be varied from 512×512 up to 1024×1024, which also changes the voxel size.

Figure 5A:
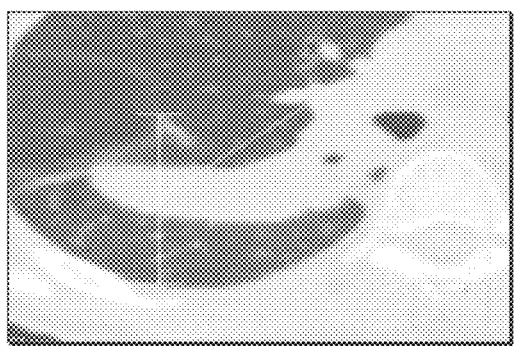
FIG. 5A-5B are images illustrating a single acquisition of a thoracic tumor using two different reconstruction algorithms.
Figure 5B:
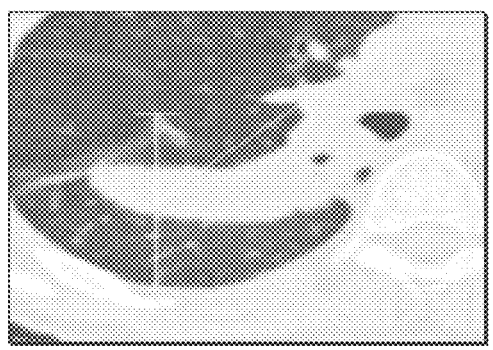
Figure 5C:
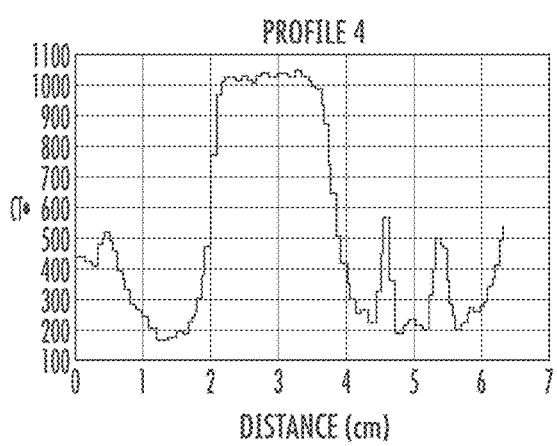
FIGS. 5C-5D are graphs illustrating the variation in Hounsfield units (Hus) or texture along the vertical paths in FIGS. 5A-5B, respectively.
Figure 5D:
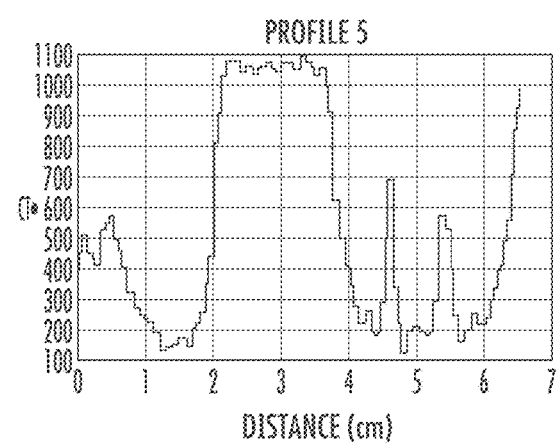

Pitch is a parameter that is frequently optimized by each scanner manufacturer so that only certain pitches are allowed for an image acquisition. These pitches are unique to each scanner, and as a result, comparing noise between scanners can only be performed by investigating images acquired using axial, as opposed to helical or spiral, acquisitions. However, helical image acquisitions are used most often in a clinical setting. HUs can also vary with reconstruction algorithm. A single acquisition of a thoracic tumor using two different reconstruction algorithms is shown in FIGS. 5A-5B. FIG. 5A shows a "standard smooth image" and FIG. 5B shows the same raw data reconstructed using a higher contrast algorithm. While this is a single data acquisition, there are significant variations in tumor texture between the two images. To appreciate the effect of these reconstruction algorithms, the profiles (in HUs) along the vertical lines are shown in FIGS. 5C-5D, respectively. Even the average HUs in the tumor are different for the different algorithms. For clinical trials, reconstruction protocols and image noise can be matched between scanners of different vendors. While the CAT phantom is a reasonable initial step to compare different scanners, more sophisticated phantoms may be required to match the effects of reconstruction algorithms. Although there can be some variation, different vendors have algorithms that are similar enough to be quantitatively comparable. Additionally, features with (a) sufficient dynamic range between patients, (b) intrapatient reproducibility and (c) insensitivity to image acquisition and reconstructions protocol can be used in the techniques described herein.

PET-CT

Figure 6A:
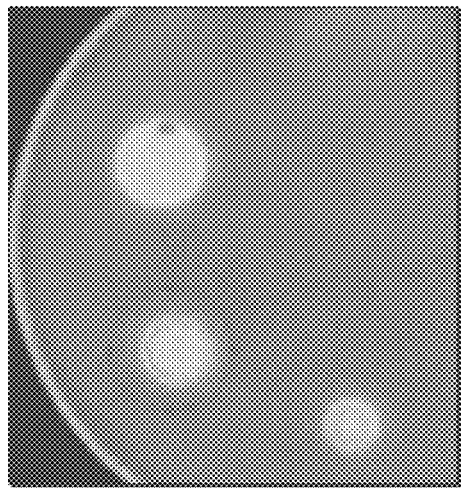
FIG. 6A is an image illustrating metabolic volume calibration of a PET scanner.
Figure 6B:
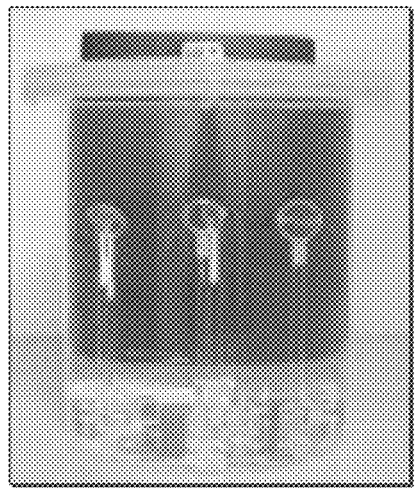
FIG. 6B is an example PET phantom.

Quantitative imaging with 2-deoxy-2-[$^{18}$F]fluoro-d-glucose (18-FDG) PET scans is a challenge because it not only requires calibration of the scanner and standardization of the scan protocol but also requires the patient and staff to adhere to a strict patient protocol. From a technical viewpoint, the main challenges are the dose calibration and the metabolic volume or volume of interest (VOI) reconstruction that depends heavily on the scan protocol and source-to-background ratio. Before a scanner is used in a quantitative manner, interinstitution cross-calibration and quality control should be implemented. FIG. 6A is a PET image illustrating a metabolic volume calibration. FIG. 6B illustrates an example PET phantom. The PET phantom includes differently sized sphere sources filled with FDG activity within a background activity. By varying the source-to-background-activity ratio, the capability of the PET scanner to reconstruct the correct sphere volume can be quantified. From a patient protocol perspective, administration issues (e.g., residual activity in syringe, paravenous administration, etc.), blood glucose level, uptake period, breathing, patient comfort and inflammation all influence the quantization of the standardized uptake value (SUV) of 18-FDG. Complying with a strict protocol such as has been proposed by the Society of Nuclear Medicine and the European Association of Nuclear Medicine is another prerequisite to quantitative PET imaging.

MRI

The signal intensities in magnetic resonance (MR) images arise from a complex interplay of inherent properties of the tissue, such as relaxation times and acquisition parameters. Therefore, it is difficult to derive information about the physical properties of tissue from MR image signal intensities alone. This is in contrast to CT images where signal intensity can be correlated with the density of the tissue. However, certain techniques, such as diffusion-weighted imaging (DWI) and dynamic contrast-enhanced (DCE) MRI, allow assessment of physiological properties of tissue. For example, the apparent water diffusion coefficient determined using DWI varies inversely with tissue cellularity. DCE can be used to extract vascular flow, permeability and volume fractions. Although both of these techniques provide quantitative information, their reliability and reproducibility remain dependent on acquisition parameters and conditions. DW images can be of low spatial resolution and are sensitive to motion and magnetic susceptibility, and the quantization is dependent on k-space trajectory, gradient strengths and b-values. DWI has been proposed as a cancer imaging biomarker, and there are efforts to develop quality control protocols. Results of the DCE MRI depend on the contrast agent dose, method of administration, pulse sequence used, field strength of the scanner and the analysis method used. Different investigators use different methods to convert DCE MRI signal intensities to contrast agent concentration. Recently, a group of the Radiological Society of North America known as the Quantitative Imaging Biomarker Alliance initiated a standardization of the protocol for DCE MRI.

MR images can optionally have the same field of view, field strength and slice thickness. Where possible, multiple sequences with, e.g. contrast enhancement such as T1-weighted, T2-weighted, diffusion, diffusion tensor, inversion recovery (STIR) or Fluid attenuated inversion recovery (FLAIR) can be obtained fromm the same patient in a single exam. By combining these data sets into unique patterns, it is possible to view the tumor as having different sub-regions (habitats) using image features, including texture, wavelets, etc. For example, there will be areas of enhancement and potentially necrosis. The tumor bed can be extracted as an expanded region around the postcontrast T-weighted image, for example. Unsupervised clustering can be used to group the data into regions using data from multiple registered sequences. The extraction of image features from those regions, including such things as their location within the tumor bed, can allow for new types of tumor characterization. It has been observed that enhancement in individual tumors can be heterogeneous and that analysis of this heterogeneity has prognostic value. The location and characteristics of such regions have the potential to provide new insights into tumor prognosis and how well it is likely to respond to targeted treatments. The opportunity to acquire images over time will allow for comparisons and contrasts between regions.

Image Data Sets

The acquisition of images is time consuming and costly. The techniques described herein focus on standard-of-care images, with the expectation that this will generate large data sets and have more clinical impact compared to more controlled and dedicated prospective image acquisitions. Radiomics benefits from large image data sets with the expectation that large numbers may be able to overcome some of the heterogeneities inherent in clinical imaging. Image data sharing across sites will be important to make large data sets available for radiomics analysis. A major use of the information extracted from images and clinical data is the development of automated prediction models. A challenge in modeling any classifier is making it robust enough for clinical use. Development of robust models requires a sufficiently robust training set.

It is possible to collect images from a plurality of sources. For example, various online repositories are available that host image data. The image data contains the image series for each patient and each series containing image slices. Large online CT image repositories include the National Biomedical Image Archive (NBIA) and the National Lung Screening Trial (NLST), hosted by the National Cancer Institute. Apart from the images, image annotations and outcomes data are also important components to share. There can be a uniform image annotation format which could be read by other users to compare with their own segmentations. This format should support multiple annotations from alternative image analysis algorithms to support higher-level processing and prediction. The image data are linked to the metadata in DICOM-format images; the metadata contain information about the acquisition, scanner and other details of the images. Currently available clinical image data which may be used for radiomics study includes the Lung Image Database Consortium, the Reference Image Database to Evaluate Response to therapy in lung cancer and others. Radiomics analyses use refined image data based on image characteristics (resolution, reconstruction and acquisition parameters) and clinical parameters (stage of disease, type of disease and outcomes).

Segmentation

Segmentation of images into VOIs such as tumor, normal tissue and other anatomical structures is a crucial step for subsequent informatics analyses. Manual segmentation by expert readers is often treated as ground truth. However, it suffers from high interreader variability and is labor intensive; thus, it is not feasible for radiomics analysis requiring very large data sets. Many automatic and semiautomatic segmentation methods have been developed across various image modalities like CT, PET and MRI and also for different anatomical regions like the brain, breast, lung, liver, etc. Though different image modalities and organ systems require ad hoc segmentation approaches, all share a few common requirements. The segmentation method should be as automatic as possible with minimum operator interaction, should be time efficient, and should provide accurate and reproducible boundaries. Most common segmentation algorithms used for medical images include region-growing-based methods (click-and-grow), level sets and graph cuts. Region-growing methods require an operator to select a seed point within the VOI. While these methods are most suitable for relatively homogenous regions, they can be user dependent and often introduce significant interobserver variation in the segmentations. We describe here some major challenges encountered while developing segmentation methods for NSCLC.

Challenges in Segmentation of Lung Tumors

Figure 7A:
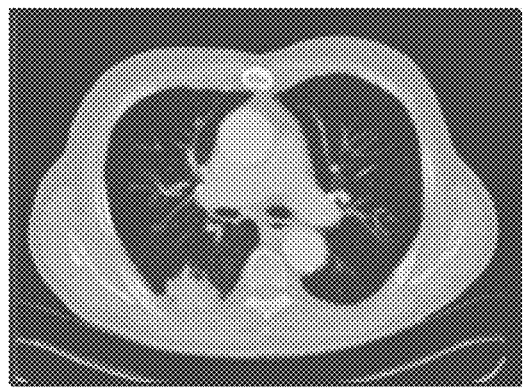
FIGS. 7A-7B are images of representative example lung tumors attached to anatomical structures like pleural wall, mediastinum or heart that are difficult to segment automatically.
Figure 7B:
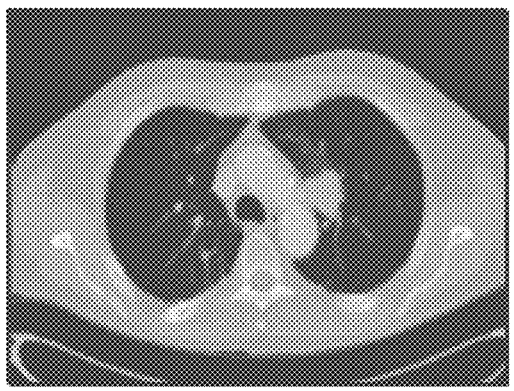
Figure 8A:
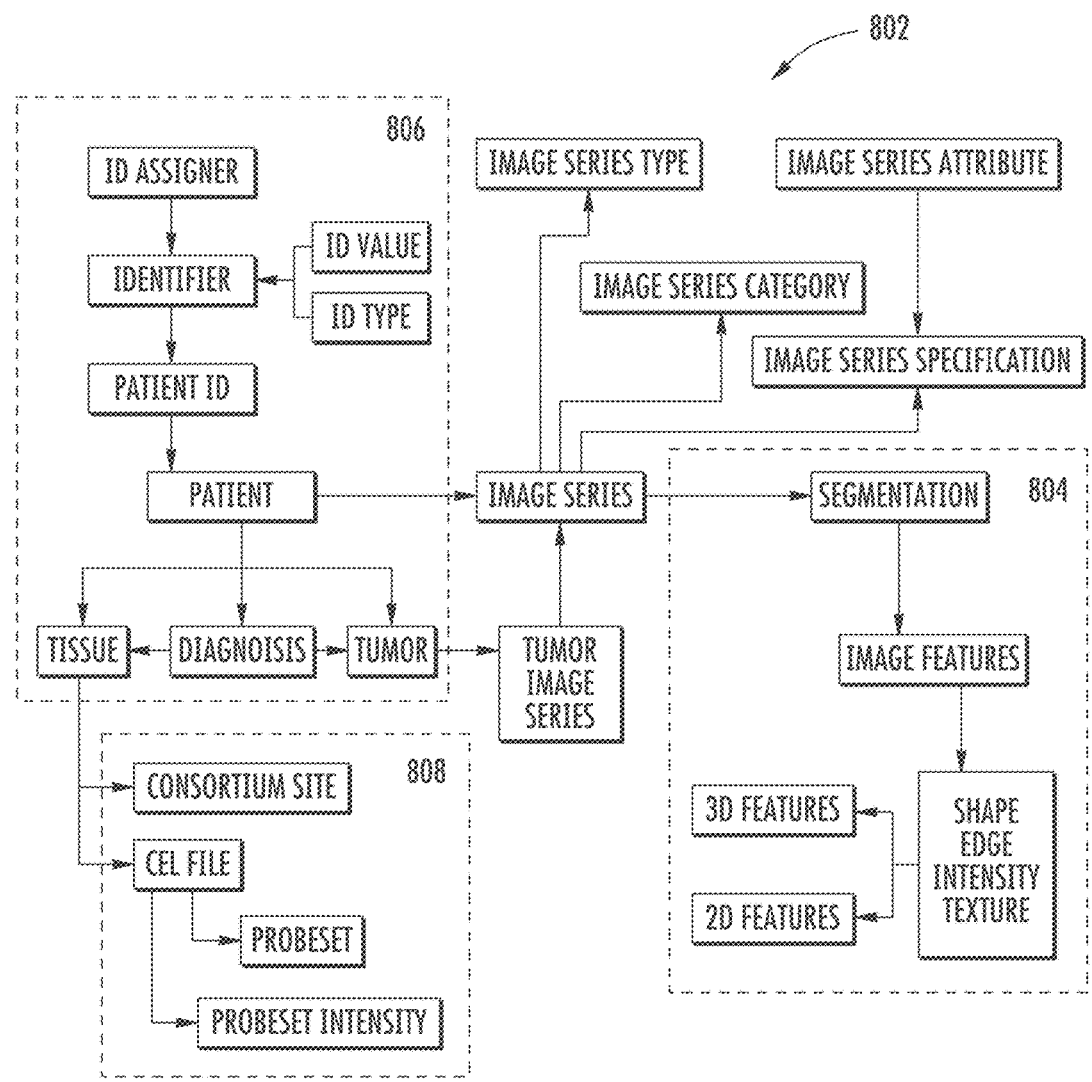
FIG. 8A is a block diagram illustrating an example architecture of a data structure for storing a plurality of radiological image records.
Figure 8B:
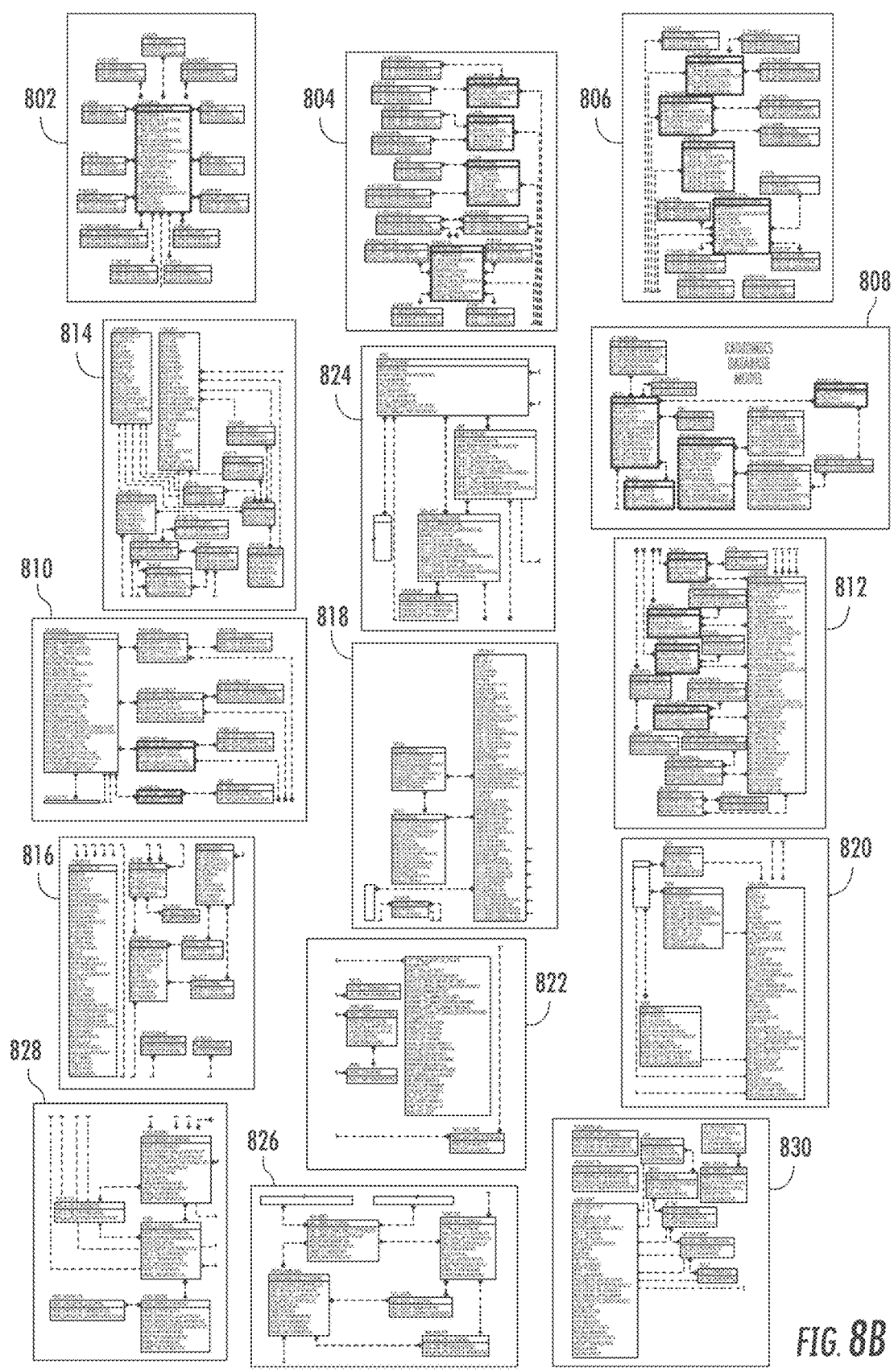
FIG. 8B is another block diagram illustrating an example architecture of a data structure for storing a plurality of radiological image records.
Figure 8C:
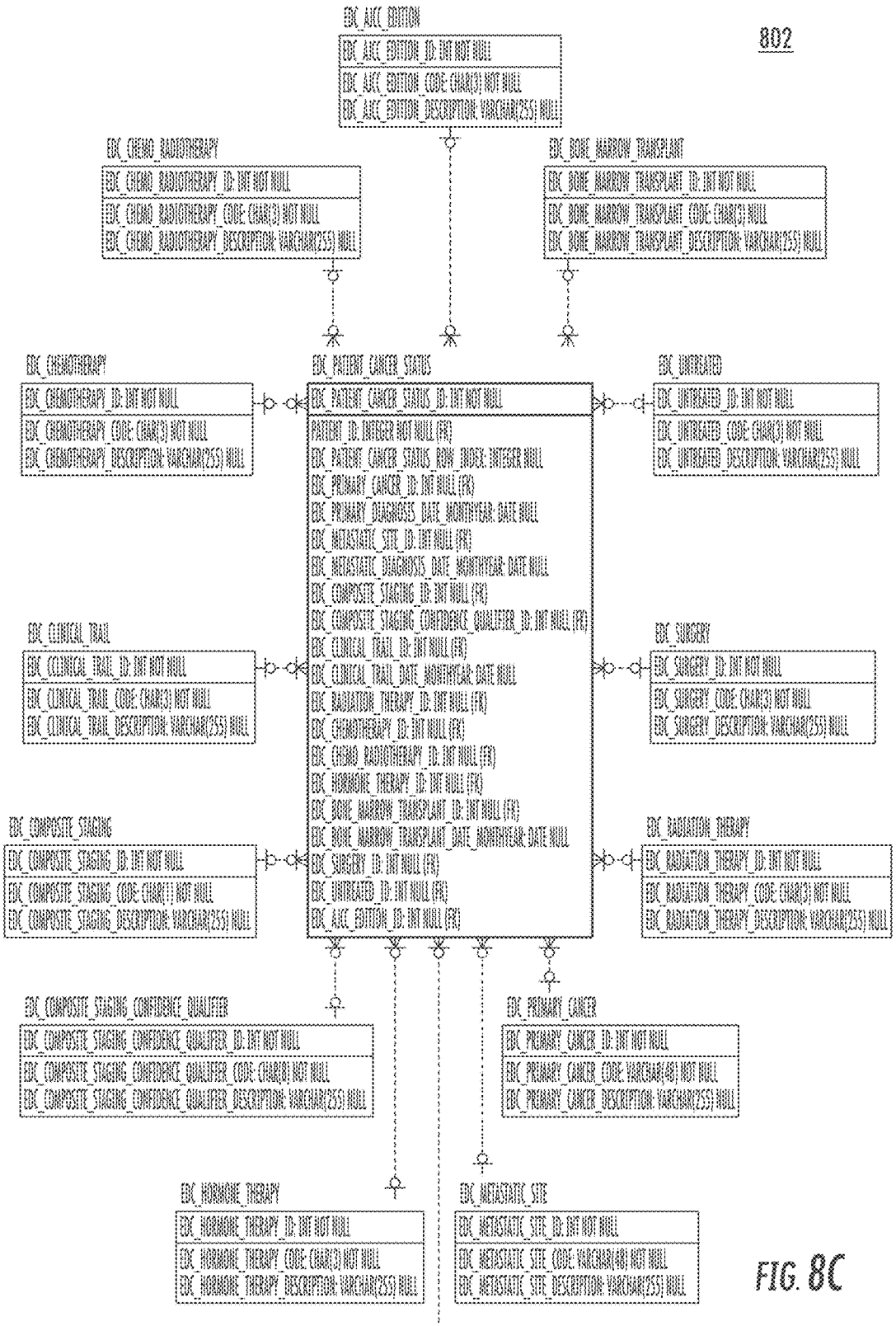
FIGS. 8C-8Q are blown up portions 802, 804, 806, 808, 810, 812, 814, 816, 818, 820, 822, 824, 826, 828 and 830 of the block diagram shown in FIG. 8B.
Figure 8D:
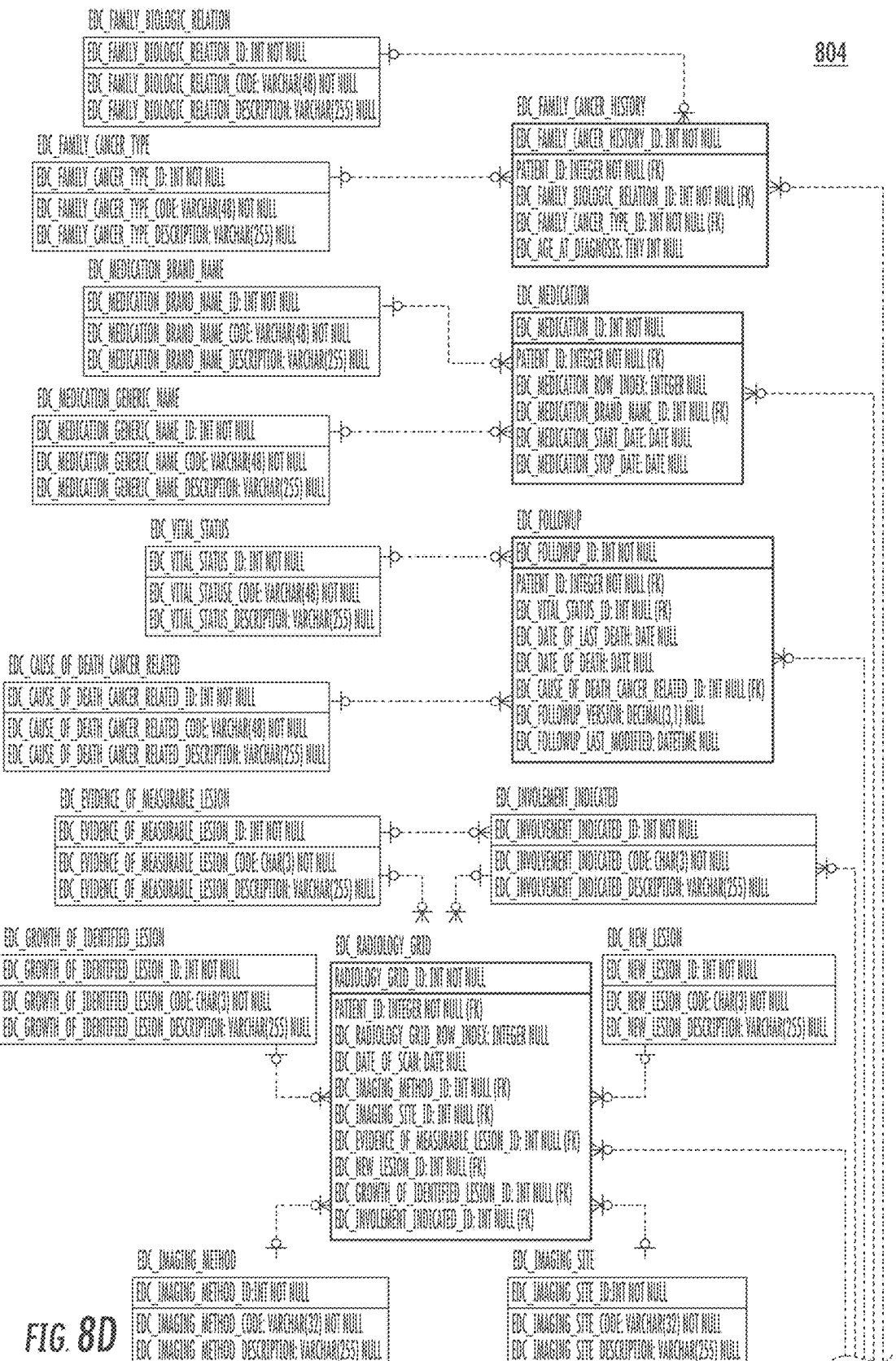
Figure 8E:
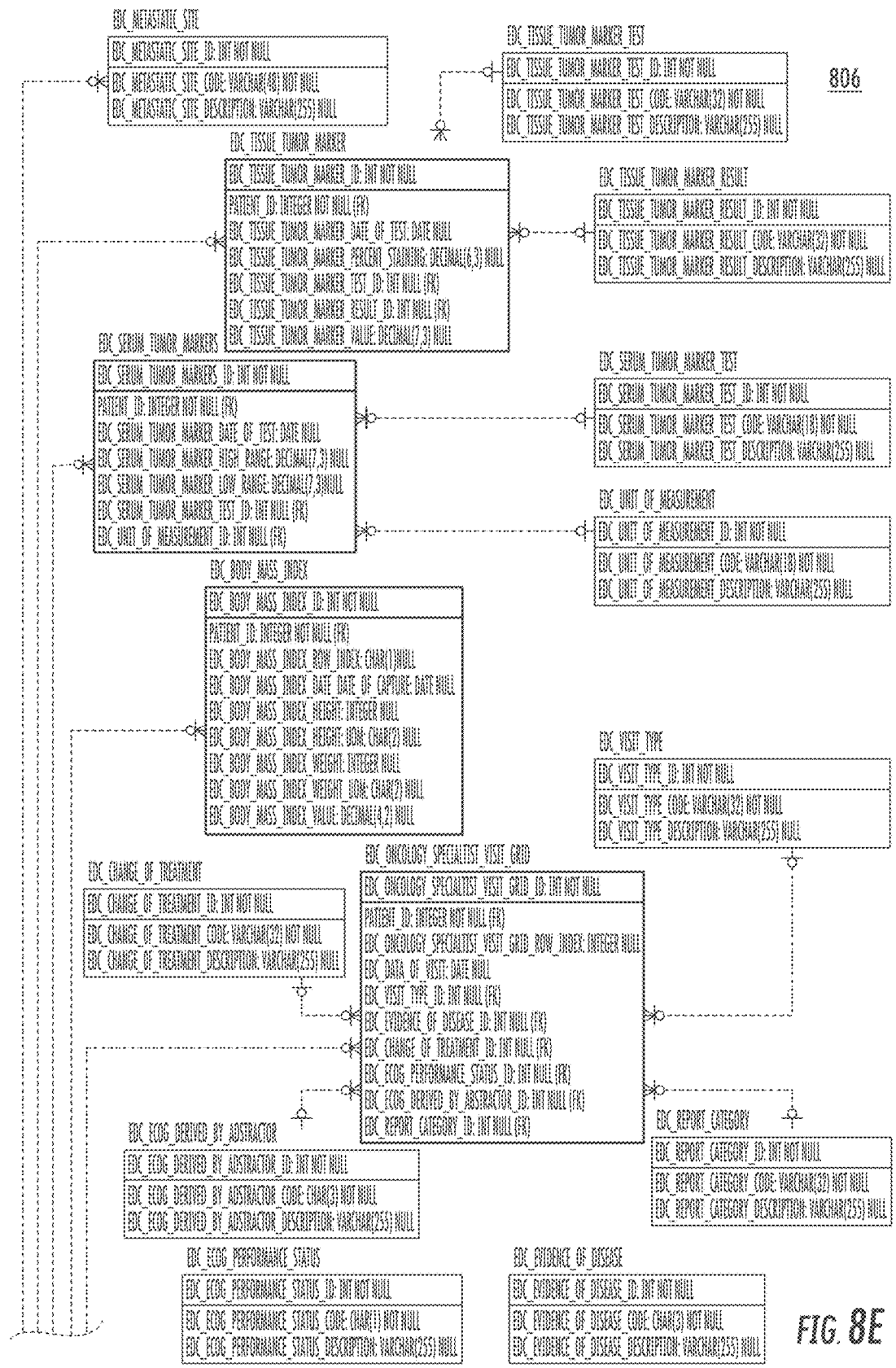
Figure 8F:
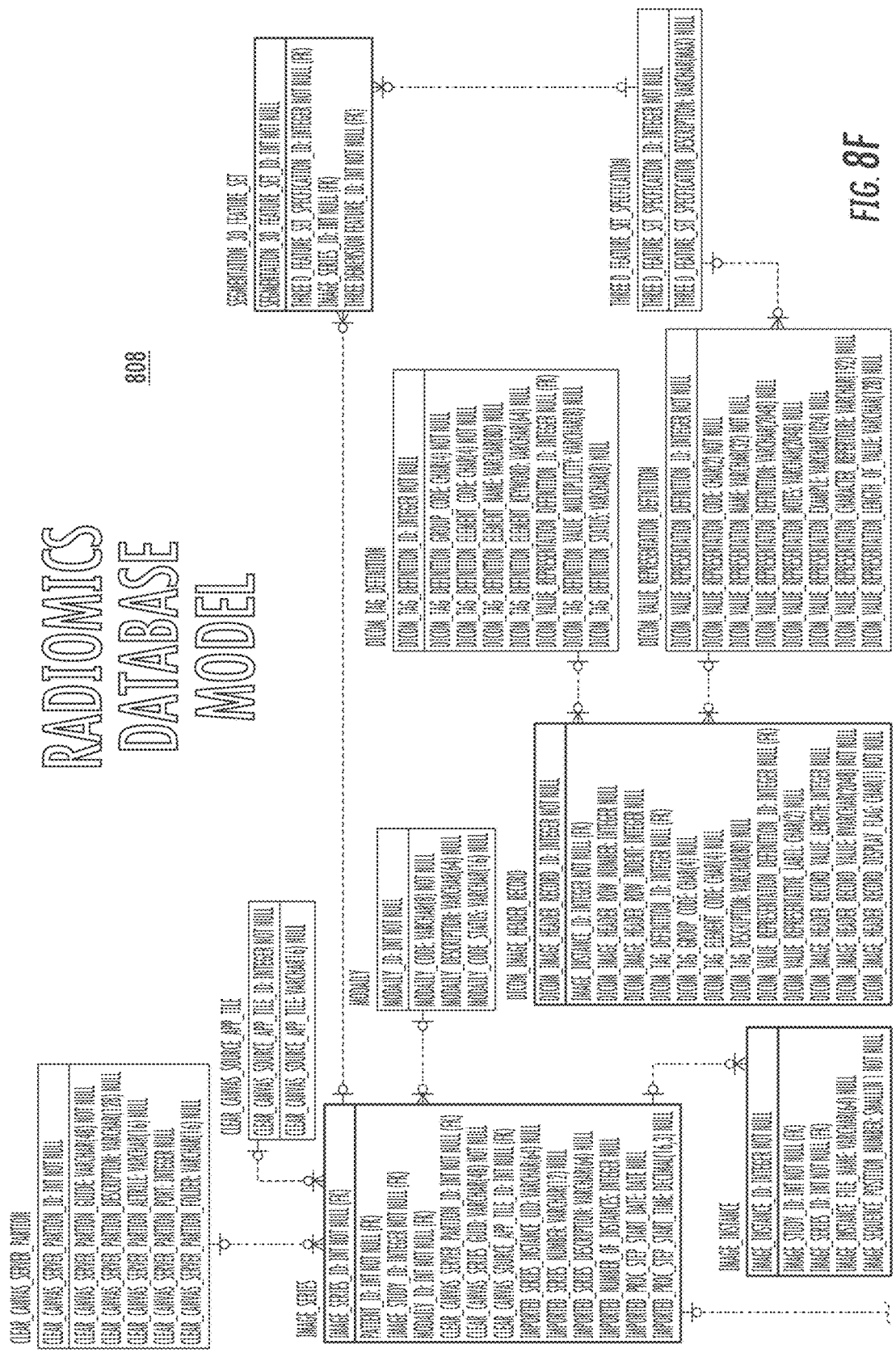
Figure 8G:
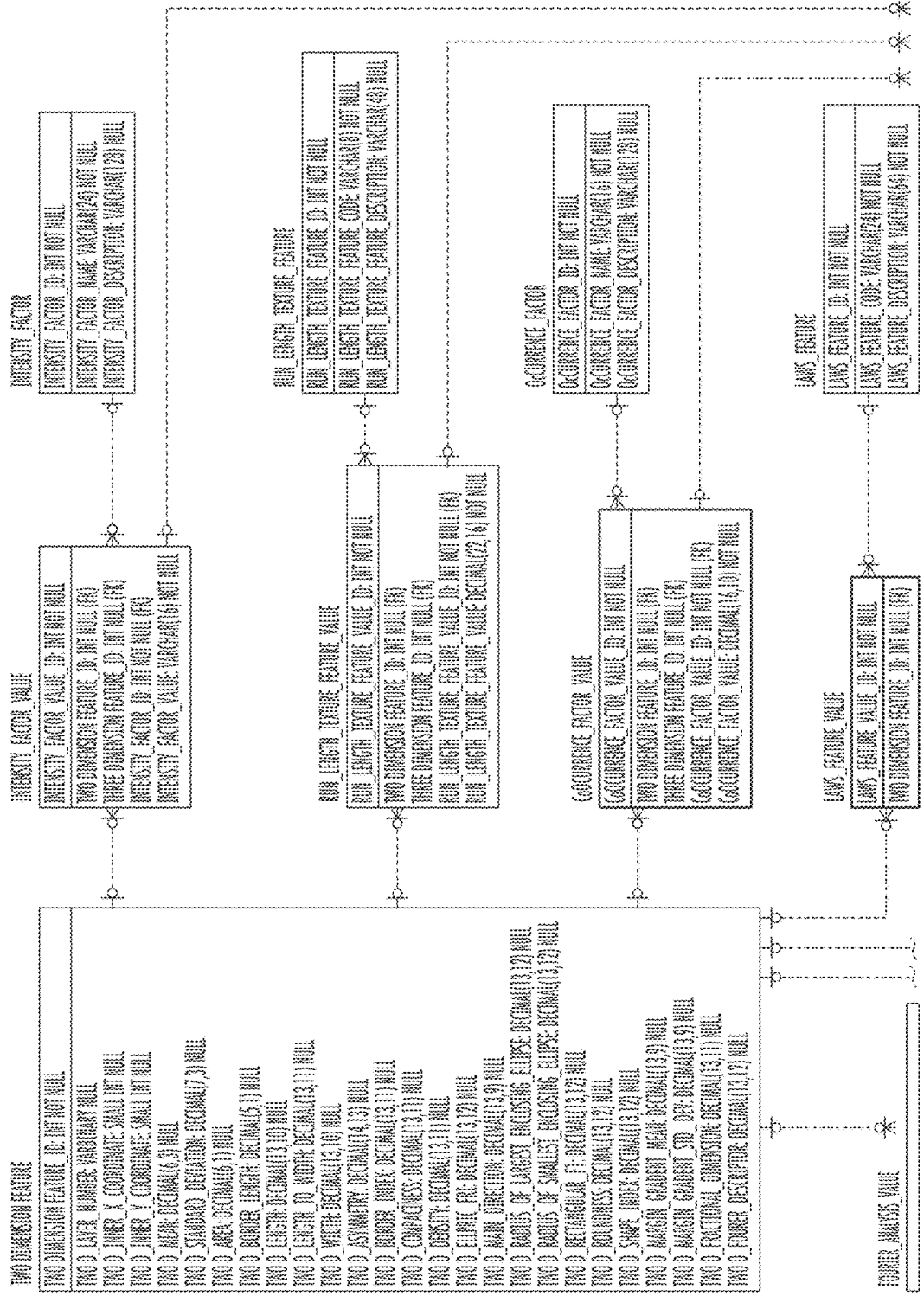
Figure 8H:
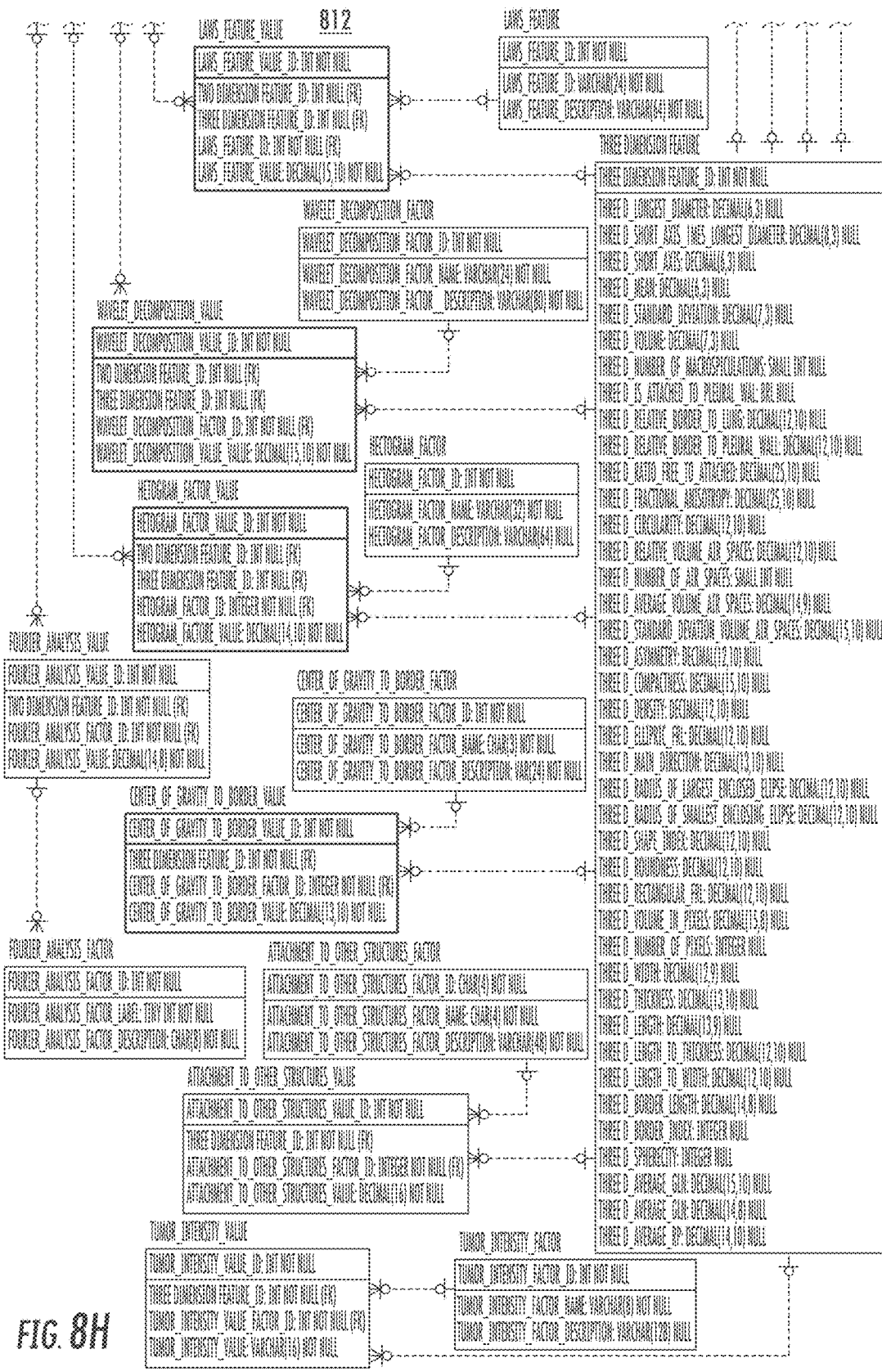
Figure 8I:
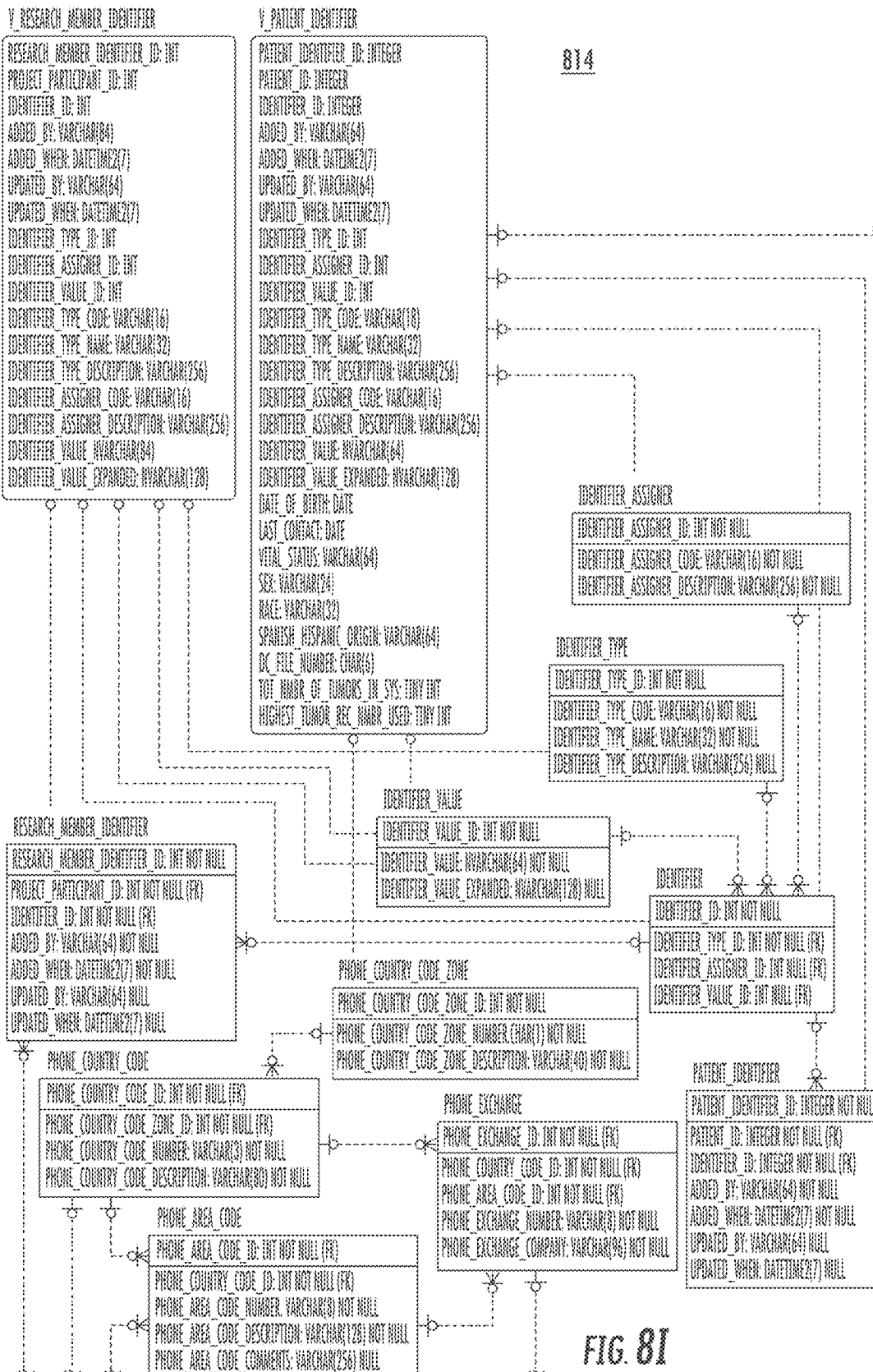
Figure 8J:
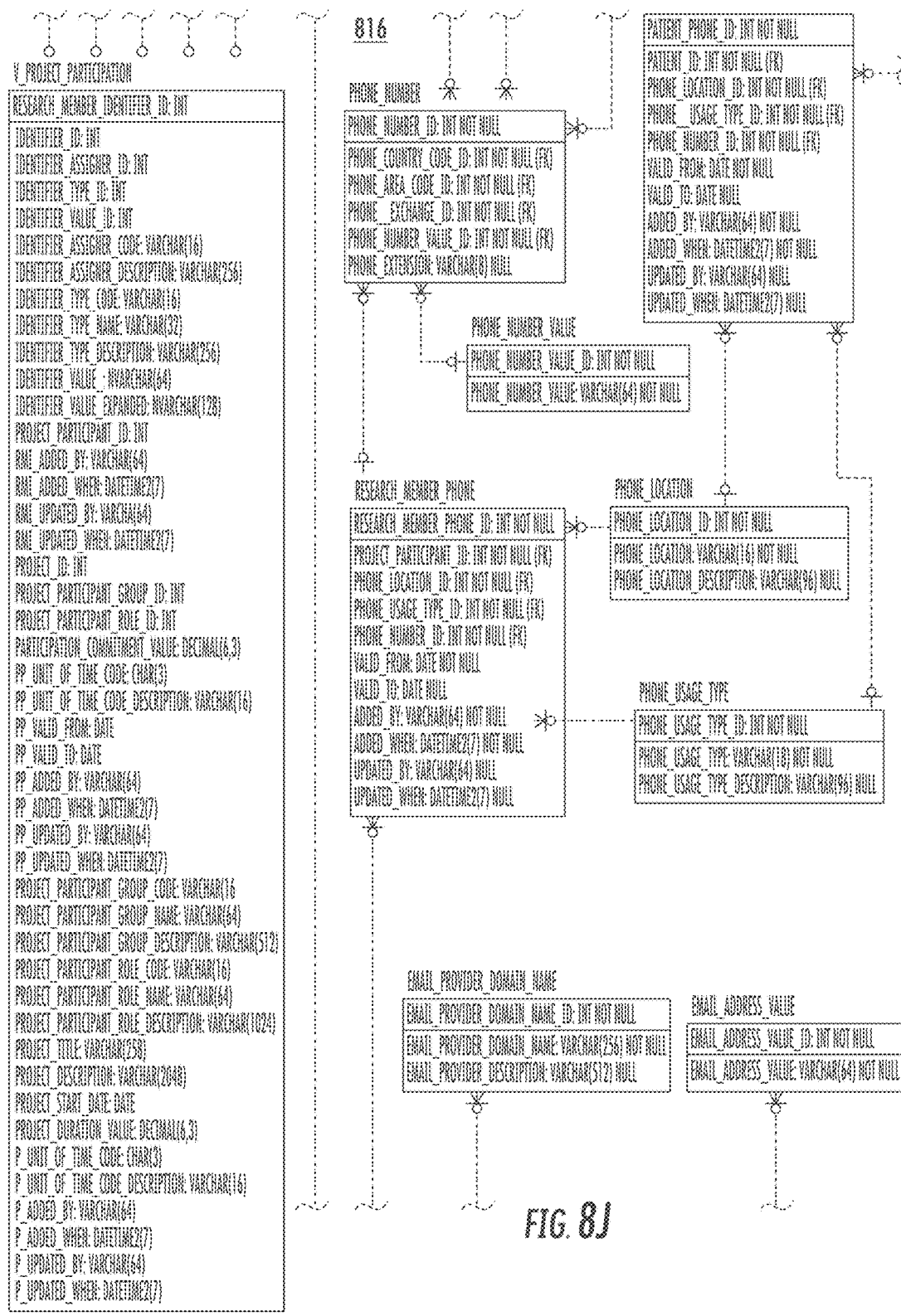
Figure 8K:
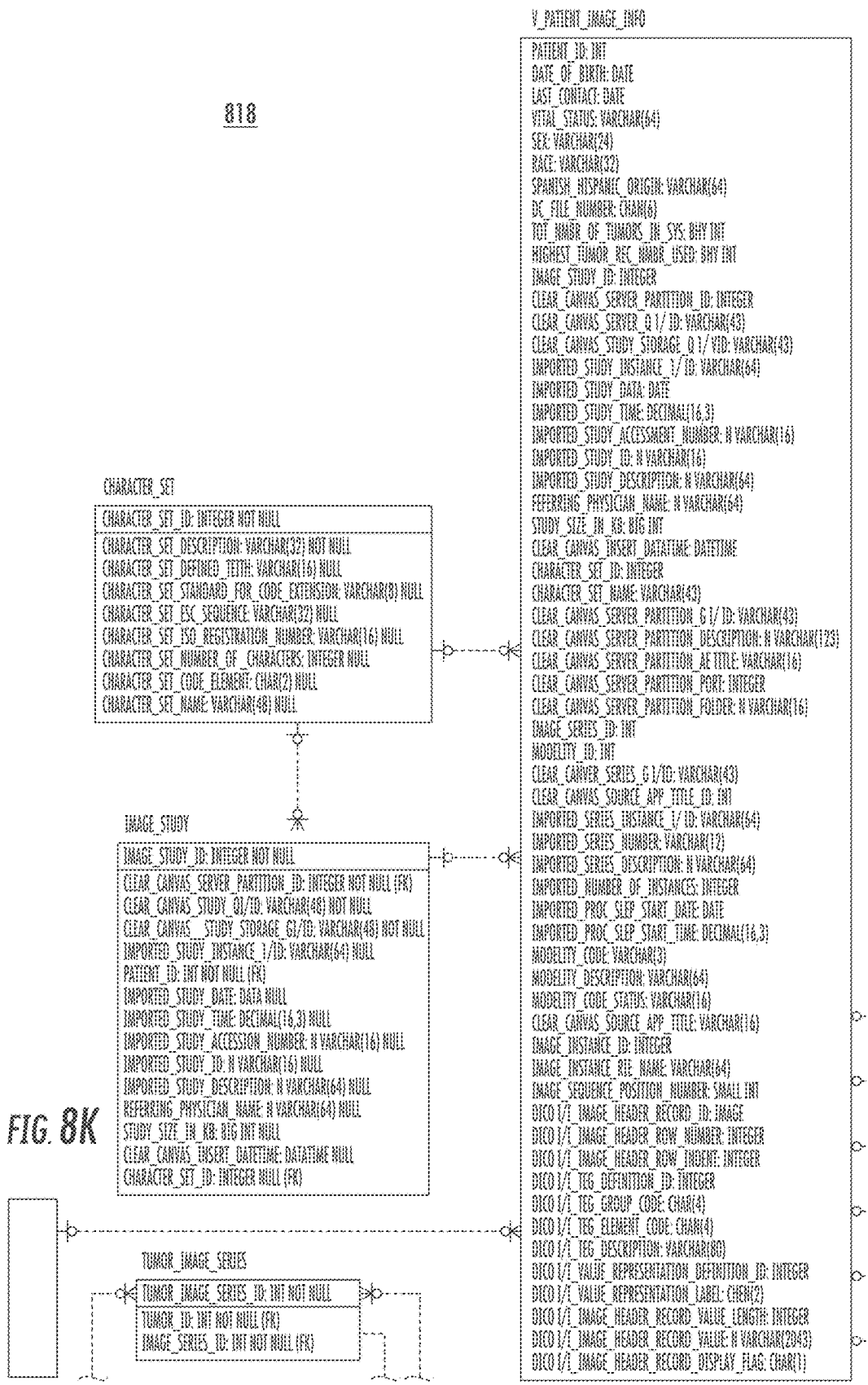
Figure 8L:
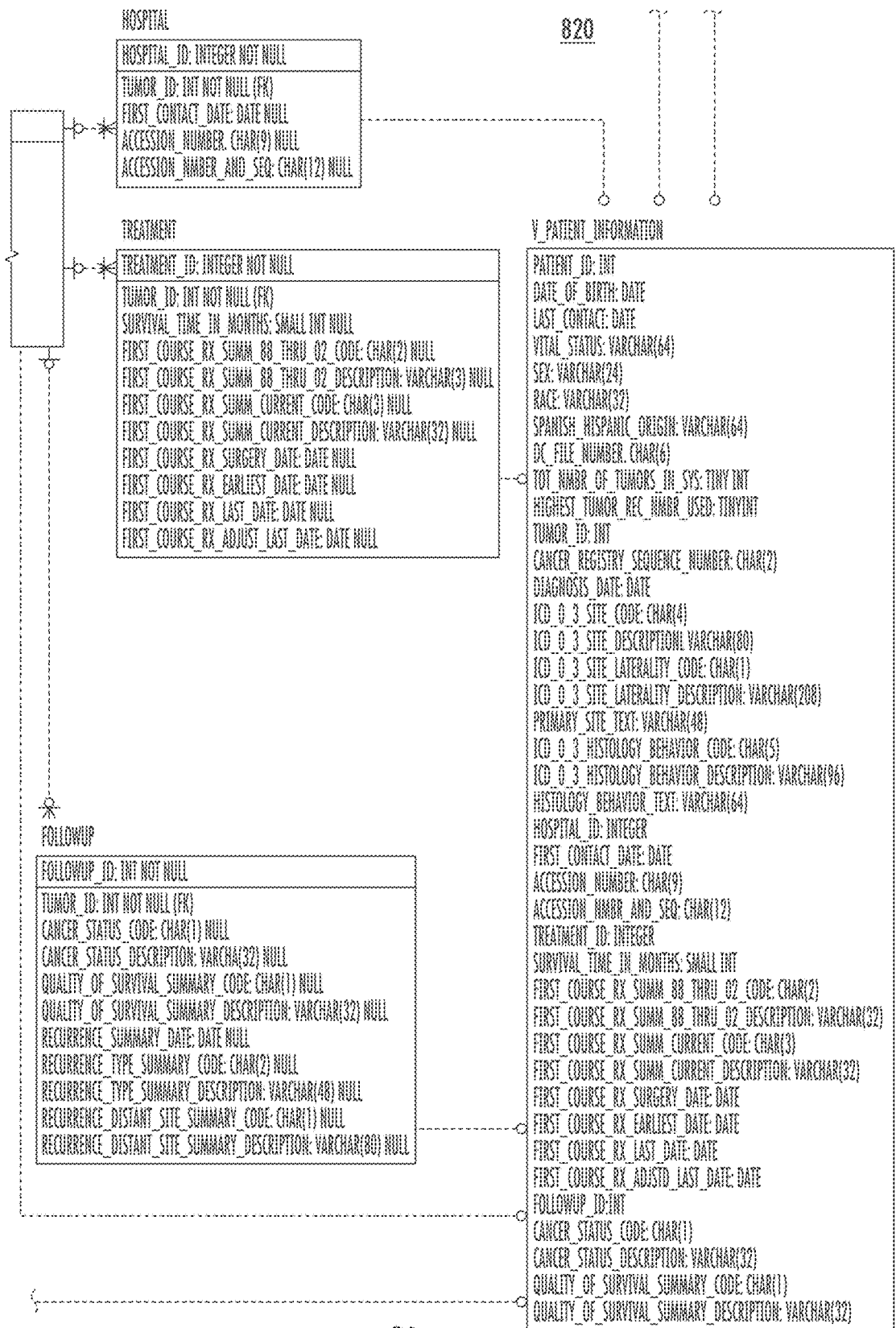
Figure 8M:
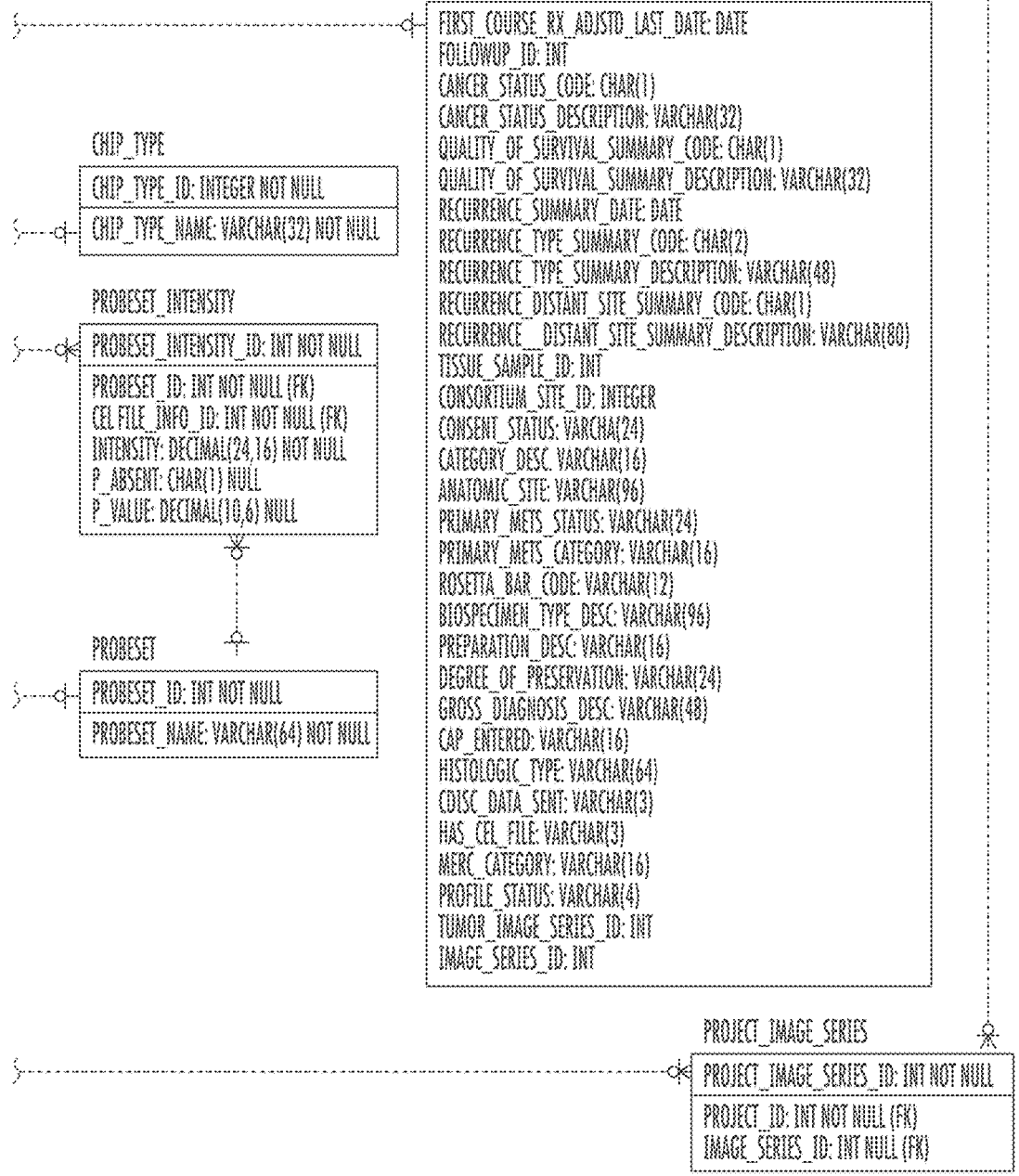
Figure 8N:
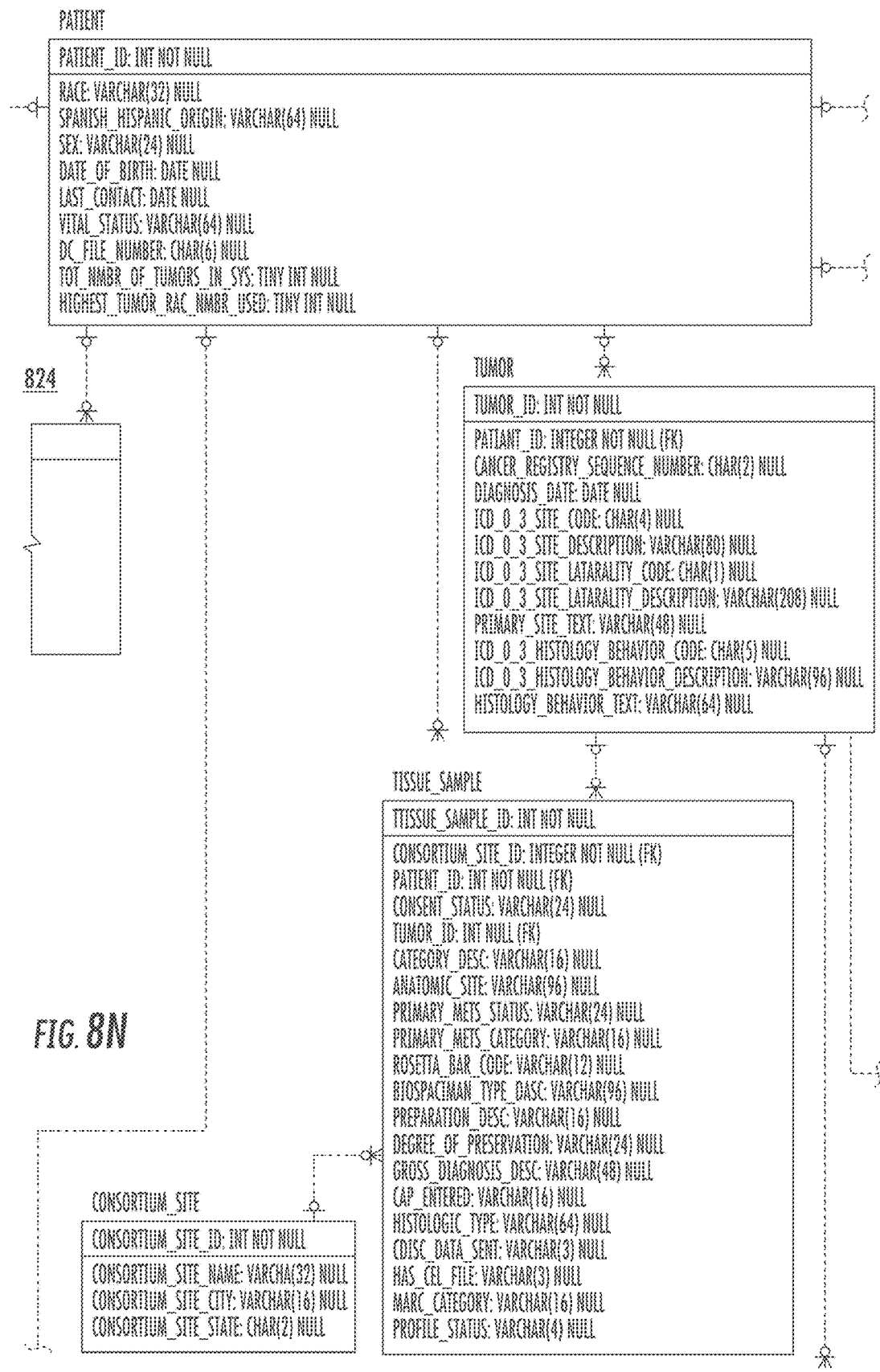
Figure 80:
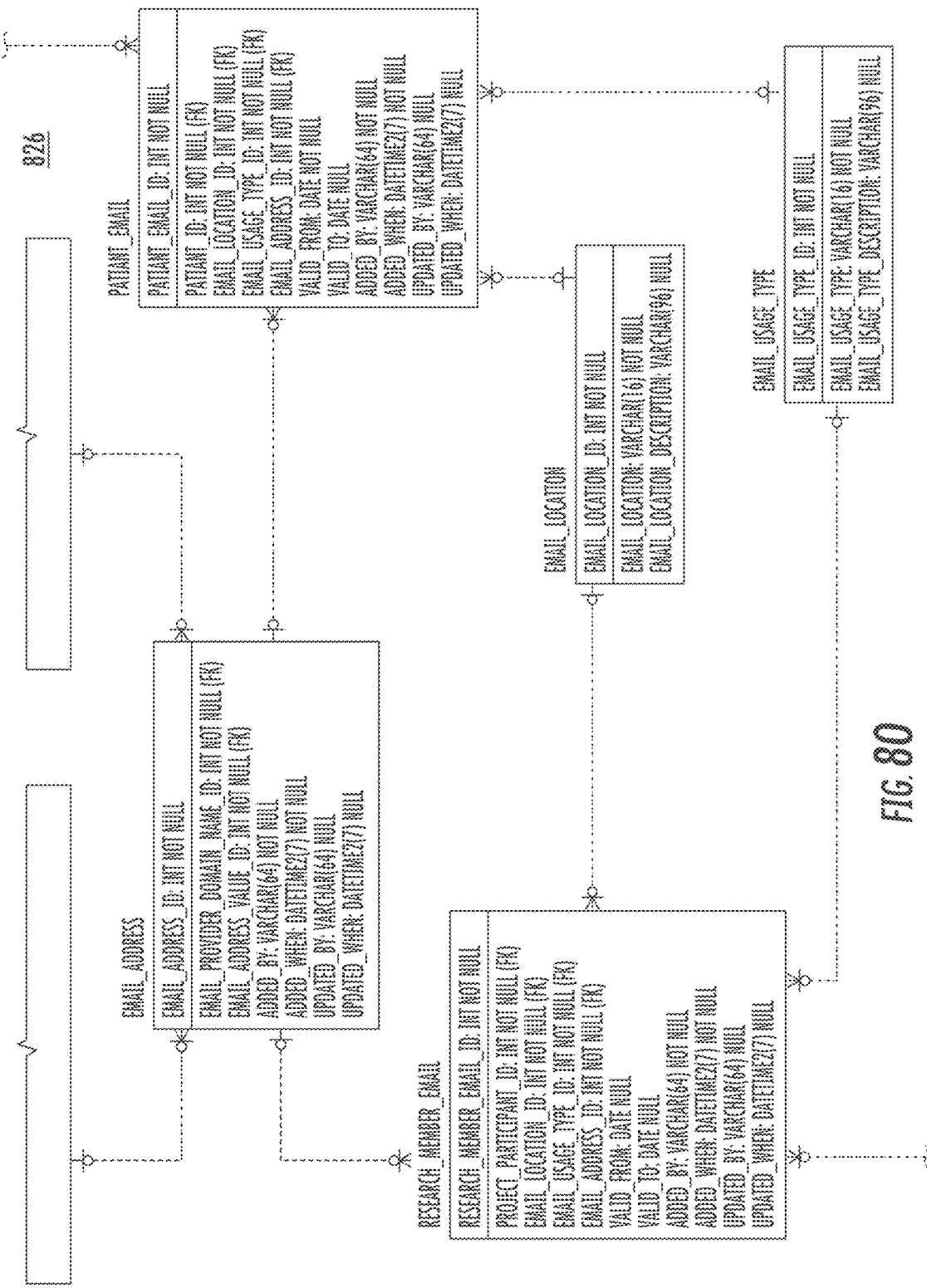
Figure 8P:
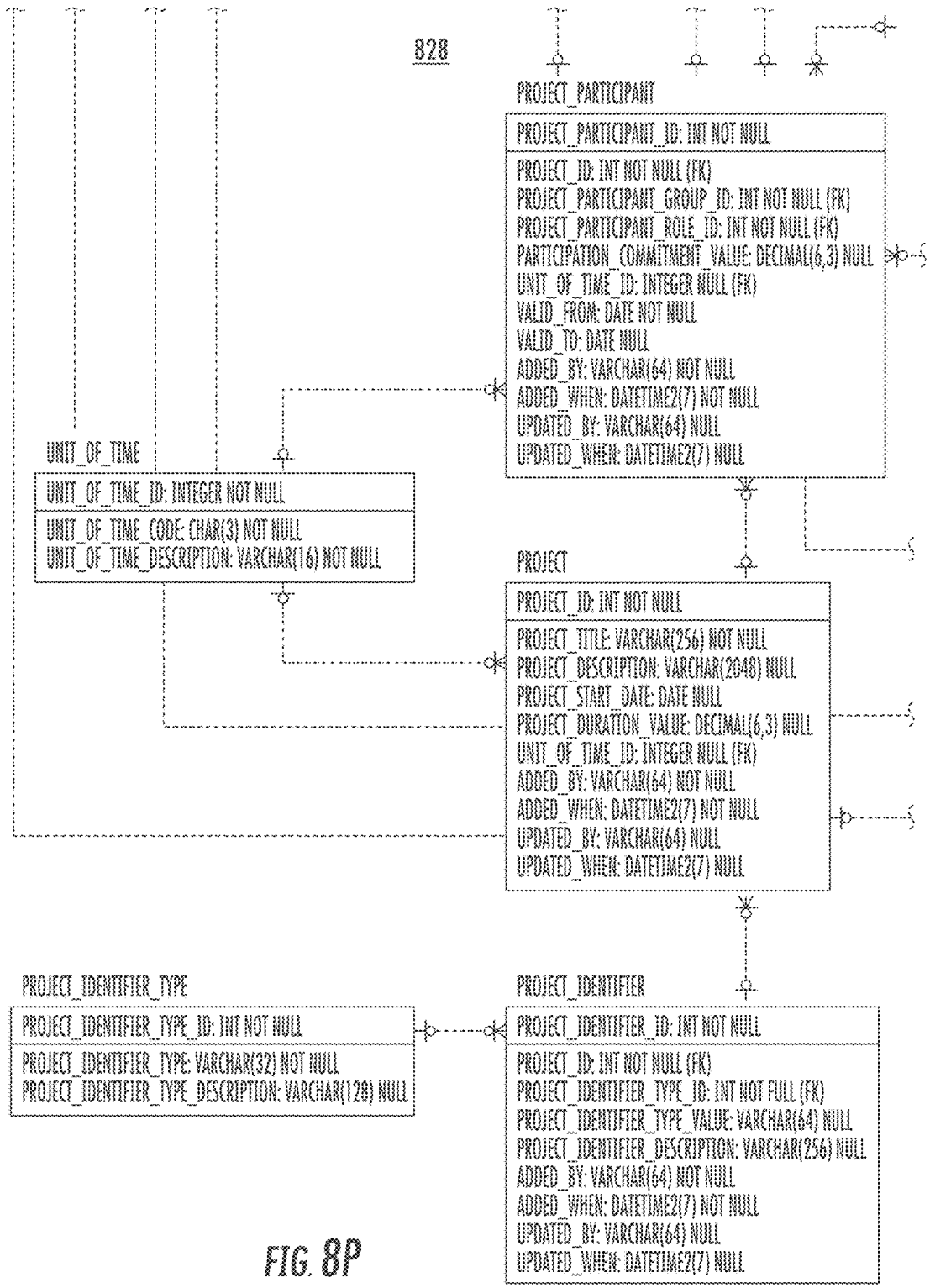
Figure 8Q:
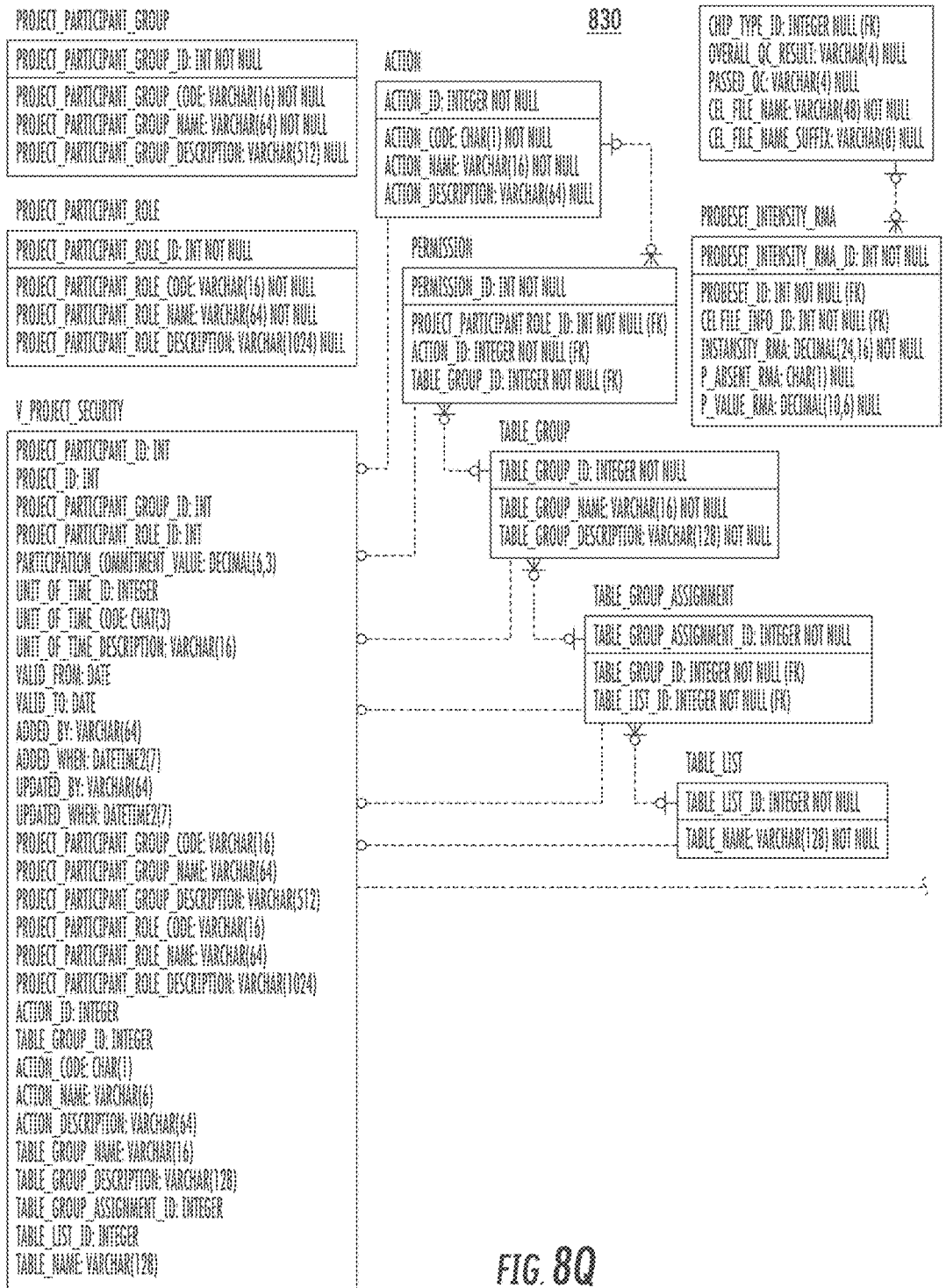

The segmentation of CT thorax images usually requires segmentation of lung fields for successive segmentation of lung nodules. Right and left lungs should be automatically segmented, which may serve as a preprocessing step. This has been achieved relatively successfully. However, in cases where high-intensity tumors are attached to the pleural wall or mediastinum, automatic segmentation may underperform. FIGS. 7A-7B are images of representative example lung tumors attached to anatomical structures like pleural wall, mediastinum or heart that are difficult to segment automatically. While using rule-based methods, automatic segmentations may fail in such cases, as evidenced by extension of lung boundaries into the mediastinum or heart. A majority of Stage I and Stage II NSCLC nodules present as homogenous, high-intensity lesions on a background of low-intensity lung parenchyma. These can be segmented with high reproducibility and accuracy. However, partially solid, ground glass opacities, nodules attached to vessels and nodules attached to the pleural wall remain difficult to segment automatically and show low reproducibility, especially for Stage III and Stage IV disease. Work is in progress to improve the automatic segmentation and reproducibility in these cases. For example, a possible solution may come from "crowd-sourcing" the solutions via "segmentation challenges": public databases for comparing segmentation results via standard metrics.

Manually traced segmentations are often used as gold standard or ground truth against which the accuracy of the automatic segmentation is evaluated. However, manually traced boundaries themselves suffer from significant inter-reader bias, and the reproducibility is low. In a large image data set and especially with slices thickness 3.0 mm or less where number of slices may be higher than 200 per patient, the option of tracing manual boundaries is time prohibitive. Therefore, it is important to have a segmentation algorithm which is automatic and reproducible. The reproducibility of a manual or automatic segmentation of tumors is a known issue. Inter- and intrareader reproducibility significantly varies. As discussed earlier, in radiomics, sources of variations come from acquisition of images, segmentation and analysis, and should be minimized.

Segmentation Algorithms

Many popular segmentation algorithms have been applied in medical imaging studies within the last 20 years; the most popular ones include region-growing methods, level set methods, graph cut methods, active contours (snake) algorithms and semiautomatic segmentations such as livewires, etc.

Region-growing algorithms are rapid, but undesired "regions" will be produced if the image contains too much noise. The level set method was initially proposed by Osher and Sethian in 1988 to track moving interfaces, and it was subsequently applied across various imaging applications in the late 1990s. By representing a contour as the zero level set of a higher dimensional function (level set function), level set method formulates the motion of the contour as the evolution of the level set function. The graph cut method is relatively new in the area of image segmentation, which constructs an image-based graph and achieves a globally optimal solution of energy minimization functions. Since graph cut algorithms try to identify a global optimum, it is computationally expensive. Another problem for graph cut is the oversegmentation.

The active contours (snake) algorithm works like a stretched elastic band being released. The start points are defined around the object which needs to be extracted. The points then move through an iterative process to a point with the lowest energy function value. The active contours algorithm requires a good initialization; it is also sensitive to noise, which may lead the snake to undesired locations. The livewire (intelligent scissor) method is motivated by the general paradigm of the active contour algorithm: it converts the segmentation problem into an optimal graph search problem via local active contour analysis, and its cost function is minimized by using dynamic programming. A disadvantage of the livewire approach is that it is semiautomatic, requiring multiple human interactions.

There is no universal segmentation algorithm that can work for all medical image applications. With proper parameters settings, each segmentation could segment the region of interest automatically or semiautomatically. However, the result of each segmentation will be quite different, and even for the same algorithm performed multiple times with different initializations, results may be variable. Hence, it is very important to develop agreed-upon metrics to evaluate segmentation algorithms.

Performance Metrics

Accuracy, reproducibility and consistency are three of the most important factors to evaluate a segmentation algorithm for medical images. However, conventional evaluation metrics normally utilize the manual segmentation provided by radiologists, which is subjective, error prone and time consuming. In the majority of cases, manual segmentation tends to overestimate the lesion volume to ensure the entire lesion is identified, and the process is highly variable. In other words, "ground truth" segmentation does not exist. Hence, reproducibility and consistency are more important than accuracy. That is, for a given a tumor, an algorithm must reproducibly provide the same segmentation results that are user independent.

The metrics for evaluation of image segmentation algorithms should address the particular characteristic of the algorithm to be compared, as automated as possible, quantitative and easily computed. Many metrics have been used, like volume, center of volume and maximum surface distance, to compare characteristics like robustness and accuracy. The Jaccard Similarity Index (SI) is the measure of the overlap of two or more volumes and is calculated as the ratio of voxel-wise intersection to union of target and reference images:

$$SI_{ab} = \frac{S_a \cap S_b}{S_a \cup S_b}, \quad (1)$$

where Sa and Sb are segmentations of target and reference images, respectively. An SI of 1.0 represents complete overlap (volume, location and shape), and 0 means no overlap. In the examples, SI between each pair of 20 independent computer-generated segmentations of individual lung tumors can be calculated and the average SI for each lesion can be reported using following equation:

$$AverageSI_i = \frac{1}{20}\sum_{m=1}^{20}\left[\frac{1}{19}\sum_{n \neq m, n=1}^{20} SI_{im,in}\right], \quad (2)$$

where $i \in [1, \#ofcases]$ is the case index, $SI_{im,in}$ is from Eqn. (1). For manual segmentations, the average SI was 0.73. For automated segmentations, the average SI was 0.93.

Feature Extraction and Qualification

Once tumor regions are defined, imaging features can be extracted. These features describe characteristics of the tumor intensity histogram (e.g., high or low contrast), tumor shape (e.g., round or spiculated), texture patterns (e.g., homogeneous or heterogeneous), as well as descriptors of tumor location and relations with the surrounding tissues (e.g., near the heart).

Tumor Intensity Histogram

Tumor intensity histogram-based features reduce the three-dimensional (3D) data of a tumor volume into a single histogram. This histogram describes the fractional volume for a selected structure for the range of voxel values (e.g., Hounsfield units for a CT scan or SUVs for an FDG-PET scan). From this histogram, common statistics can be calculated (e.g., mean, median, min, max, range, skewness, kurtosis), but also more complex values, such as metabolic volume above an absolute SUV of 5 or the fraction of high-density tissue measured with CT. Such threshold values have shown promise in developing classifier models, and optimum thresholds for a given task can be identified with receiver operator characteristic (ROC) analyses. As the outcome (e.g., time to recurrence) to which the threshold is being compared can also have a variable threshold, 3D ROC approaches have been developed to represent a surface to optimize both the biomarker and the outcome thresholds.

Shape-based Features

Quantitative features describing the geometric shape of a tumor can also be extracted from the 3D surface of the rendered volumes. For example, the total volume or surface area can be an important characteristic. Also, the surface-to-volume ratio can be determined, where a speculated tumor has a higher value than a round tumor with a similar volume. Furthermore, descriptors of tumor compactness and shape (sphericity, etc.) can also be calculated.

Texture-based Features

Second-order statistics or co-occurrence matrix features can be used for texture classification and are widely applied in medical pattern recognition tasks. The basis of the co-occurrence features lies on the second-order joint conditional probability density function $P(i,j;a,d)$ of a given texture image. The elements $(i,j)$ of the co-occurrence matrix for the structure of interest represent the number of times that intensity levels $i$ and $j$ occur in two voxels separated by the distance $(d)$ in the direction $(a)$. Here, a matrix can be selected to cover the 26-connected directions of neighboring voxels in 3D space. The matrix size is dependent on the intensity levels within the 3D structure. Subsequently, from this conditional probability density function, features can be extracted, e.g., describing autocorrelation, contrast, correlation, cluster prominence, cluster shade, cluster tendency, dissimilarity, energy, homogeneity, maximum probability, sum of squares, sum average, sum variance, sum entropy or difference entropy, etc. Furthermore, gray level run length features, derived from run length matrices and using run length metrics can be extracted. A gray level run is the length, in number of pixels, of consecutive pixels that have the same gray level value. From the gray level run length matrix, features can be extracted describing short and long run emphasis, gray level nonuniformity, run length nonuniformity, run percentage, low gray level run emphasis and high gray level run emphasis. As expected, such analyses can generate hundreds of variables, some of which may be redundant. Thus, it is important to assess the redundancy of these data using covariance.

Feature Qualification

As described above, a large number of image features can be computed. However, all these extracted features may not be useful for a particular task. In addition, the numbers of extracted features can be higher than the number of samples in a study, reducing power and increasing the probability of overfitting the data. Therefore, dimensionality reduction and selection of task-specific features for best performance are necessary steps. Different feature selection methods can be used for this purpose and may exploit machine learning or statistical approaches. Dimensionality reduction can also be achieved by combining or transforming the original features to obtain a new set of features by using methods like principal component analysis (PCA). In addition to feature selection for informative and nonredundant features, high stability (i.e. high reproducibility and low inter-observer variability) of the features is important in the development of clinical biomarkers, which requires the availability of a test-retest data set as well as VOI definitions by multiple observers.

To reduce the dimensionality of the feature space, it is possible to combine different ad hoc methods that are agnostically applied to the behavior of the features themselves prior to evaluating their ability to develop predictive models. Thus, features are evaluated to fulfill three main requirements: highly stable reproducible, informative and nonredundant. Three methods can be applied in serial manner, where the methods were applied successively to select features. The resulting features of one method were used as input to the next. First, using a test-retest lung CT image data set, highly reproducible features were selected based on concordance correlation coefficient (CCC), with a cutoff of 0.85 for high reproducibility. Subsequently, the CCC-prioritized features were analyzed for dynamic range, calculated as the ratio of scalar biological range to the test-retest absolute difference. Features showing high dynamic range were considered to be informative. A dynamic range of, e.g., 0 to 1 can be arbitrarily used as a cutoff, although features with lower dynamic range may also be informative. Finally, the redundancy in the features, selected after passing through reproducibility and dynamic range requirements, can be reduced by identifying highly correlated features based on correlation coefficients across all samples. Correlation coefficients greater than 0.95 are considered to be highly redundant and thus can be combined into a single descriptor. In a test set, the serial application of these three methods was able to reduce a set of 327 quantitative features to 39 that were reproducible, informative and not redundant. More features could be added by relaxing the dynamic range threshold, which was arbitrarily set at 100. These selected features can also be used to develop classifier models based on machine learning algorithms to improve the performance.

These quantitative features will then form the basis to answer prognostic and predictive questions to response to treatment or surgery. In the short listed features by feature reduction methods or exhaustive search methods best pairs (e.g., up to 5 dimensions) will be obtained. These multiple pairs will be then used to as a voting scheme to be predictive of outcome or prognosis. The accuracy of such prediction will be reported in level of confidence percentage (0 to 100%).

An integrated analysis of test-retest and inter-observer stability was performed for a total of 106 PET derived imaging features in NSCLC patients. In a test-retest cohort, tumor volumes were defined by a threshold of the maximum uptake value within the tumor. In an inter-observer cohort, tumor volumes were independently manually delineated by five observers, blinded to each other. For every feature, test-retest and inter-observer stability was assessed with the intra-class correlation coefficient (ICC) and the coefficient of variability, normalized to mean and range. Using an arbitrary cut-off of 0.80 for ICC, the majority of assessed features had both a high test-retest (71%) and inter-observer (91%) stability. Feature rankings based on test-retest and inter-observer stability index were furthermore found to have good overall concordance, based on rank correlation.

In another test set with CT imaging of NSCLC patients, 56 radiomic features were derived from the 3D-tumor volumes defined by three independent observers twice using a semi-automated approach in 3D-Slicer, and compared to manual slice-by-slice delineations of five independent physicians in terms of intra-class correlation coefficient (ICC) and feature range. Features extracted from 3D-Slicer segmentations had significantly higher stability and smaller, but overlapping, range compared to features extracted from the manual segmentations. 3D-Slicer segmented tumor volumes provide a better alternative to the manual delineation process, as they are more robust for quantitative image feature extraction. Although results are specific for 3D-Slicer, semi-automated, or automated delineation methods might be more reliable for quantitative image feature extraction and image data mining research in large patient cohorts.

In two other cohorts, test-retest and inter-observer (independent manual tumor delineations by five observers) stability was determined for 440 radiomic features. The 100 most stable features, which were determined by averaging both stability ranks, were selected. To remove redundancy within the radiomic information, the single best performing feature was selected for each of four pre-defined feature groups (i.e. intensity, shape, texture and wavelet based), and combined into a multivariate radiomic signature. Each feature in the resulting signature thus had a high prognostic value, as well as a high test-retest and inter-observer stability.

Databases and Data Sharing

Deidentification

To follow the principle of providing the minimum amount of confidential information (i.e., patient identifiers) necessary to accommodate downstream analysis of imaging data, raw DICOM image data can be stripped of identified headers and assigned a deidentified number. Maintaining deidentified images and clinical data is an important patient privacy safeguard. In the context of DICOM images, Supplement 142 from the DICOM Standards Committee provides guidance in the process of deidentifying images, including pixel-level data. Software packages, including NBIA, implement these standards. Likewise, molecular data can be deidentified using a similar approach. However, identifiers must be linked between imaging, molecular data and clinical data in order to build classifier models. This can be achieved through institutional review board approval or through the more expedient use of an "honest broker." The clinical data are deidentified by removing personal identifiers (including medical record numbers, patient names, social security numbers and addresses) and providing calculated interval-based survival times instead of actual dates which are also personal identifiers. The approach taken within our radiomics effort is to avoid the use of identified imaging or clinical data unless specifically required. This also facilitates the sharing of data within and across institutions since the deidentification occurs at the creation of the data set.

An Integrated Radiomics Database

The goal of radiomics is to link the image features to phenotypes or molecular signatures, and this requires development of an integrated database wherein the extracted qualitative features (and optionally the images) are linked to clinical and molecular data. FIG. 8 is a block diagram illustrating an example architecture of a data structure for storing a plurality of radiological image records. For example, a high-level database schema capturing the following data types is shown in FIG. 8: image types (802), image features (804), patient/clinical (806) and molecular (808) data. Each box represents a set of normalized tables. This schema supports multiple tumors for one patient, with multiple images series, using multiple segmentations generating different image features.

The use of such a database must also be integrated in the workflow starting from image retrieval and calculation of image features up to the joint analysis of image features, clinical data and molecular data. Furthermore, as part of a larger network of quantitative imaging sites, it is also desirable to be able to exchange data according to an evolving set of standards.

Image Storage

Using clinical Picture Archiving and Communications Systems (PACS) systems is not amenable for research projects. First, the clinical system is used for operational purposes, and introducing additional Input/Output (I/O) load and increased storage could negatively impact clinical care. Second, the requirements between research and clinical systems are different and often incompatible. The research image storage server needs to be fully integrated with the downstream data, including molecular and clinical research data. If the imported DICOM images contain Medical Records Numbers, these need to be linked to other clinical data that are stored on other systems, and then the DICOM headers will be deidentified (e.g., patient name). This allows for transparent merging of clinical data across systems. In a research setting, some of the analyses or imaging feature generation software packages also need direct access to the DICOM images. Having direct access to the file system where the images are stored makes it possible to create project folders, with all images selected for a specific project, which are specific for the software used for the image feature extraction.

Integration to Create a Simple Work Stream

In a research setting, it is common that several different software packages are used for image analysis (e.g., 3D-Slicer, Definiens Developer, Medical Imaging Toolkit [MITK]) and statistical analysis (e.g., R, SAS, Stata, matlab, mathematica). Many of these software packages may be developed by industry, in-house or by other academic groups. This requires importing data from analysis projects using these software packages in a simple way without sacrificing data integrity. This can be achieved by having the application directly reading working directories and/or results files from the software used. If unique tags have been used when creating image filenames, these data can be linked with the right image and downstream clinical and molecular data.

Integration of Clinical and Molecular Data

Integrating data across systems is always a challenge in large settings. The application needs to integrate the data from several systems, such as outcomes and demographic data (Cancer Registry), clinical trial data (e.g., Oncore) or other systems that store clinical and patient information. The manual input of such data should be kept to a minimum through the use of an extract, transform and load tool that captures the physical metadata information to maintain data provenance and minimizes the risk of human errors. The use of a well-developed data dictionary with extensive metadata is essential when integrating data across systems. Therefore, a new data warehouse model that incorporates the metadata layer into the data model, including a comprehensive data dictionary along with calculated data quality attributes such as completeness, accuracy and consistency, can be used.

This new data structure can be specifically designed to provide easy semantic integration of internal data from multiple heterogeneous source systems as well as provide an easy solution for harmonizing clinical, molecular and imaging data with external members of the quantitative imaging network. Along this path, it has also been important to ensure that the RDB structure and semantics are compatible with those from other institutions and (inter)national data bases.

Reporting and Exporting the Data

Advanced statistical analyses of radiomics data require tools such as R, SAS, or MATLAB. The application must be able to export data in such a way that it minimizes any need for processing of data outside the application and thus keeping the data aligned and correct. Longitudinal studies add an extra layer of complexity with the potential need of reporting changes over time, such as imaging features or clinical parameters. A flexible selection of which data should be included and in which format the data should be exported is important.

Statistical and Radioinformatics Analysis

Analysis within radiomics must evolve appropriate approaches for identifying reliable, reproducible findings that could potentially be employed within a clinical context. Applying the existing bioinformatics "toolbox" to radiomics data is an efficient first step since it eliminates the necessity to develop new analytical methods and leverages accepted and validated methodologies. Radiomics-specific analysis issues will exist, as in any field; therefore, an important step in achieving consensus on appropriate analysis and evaluation techniques requires availability of real-world data. The goals of the Quantitative Imaging Network (QIN) in providing infrastructure to effectively share radiomics data will enable the further development of methodology and best practices within the field.

Some of the more significant methods or developments from the bioinformatics toolbox include (a) multiple testing issues, (b) supervised and unsupervised analysis and (c) validating biomarker classifiers. Another important analytical consideration is the incorporation of clinical and patient risk factor data since they may have a causal effect or correlation with image features or they may confound statistical associations. Thus, synergizing biostatistics, epidemiology and bioinformatics approaches is necessary to build robust, parsimonious and clinically relevant predictive models relating image features to phenotypes/end points or gene-protein signatures.

High-dimensional Biomarker Discovery and Validation

The field of high-dimensional biomarker discovery and validation has evolved rapidly over the past decade since some of the earliest microarray-based results were reported. In particular, these advances have prompted many studies to address clinical prediction (e.g., prognosis, response to therapy). Many of the lessons learned and tools developed within this field are immediately relevant to the analysis of radiomics data sets.

Multiple Testing

Many of the significant developments within the field of so-called "large-p, small-n" data analysis problems are robust methods for accommodating multiple testing issues. In many data sets in these areas, it is not unusual to test the significance of tens of thousands of variables (p=50,000) using a univariate test (e.g., a t test) across 50 samples (n=50). Any single test may have a low expected false-positive rate; however, the cumulative effect of many repeated tests guarantees that many statistically significant findings are due to random chance. The false positives (type I errors in statistics) are controlled using an appropriate P value threshold (e.g., P<0.05) in the case of single test. However, performing 50,000 tests creates serious concerns over the accumulated type I error from such an experiment. This multiple testing problem has been addressed in statistics in many ways; however, the most familiar, and conservative, Bonferroni corrections severely limit the power of the test in the 50,000-test experiments. False discovery rates have been developed to provide more reasonable error estimates. Incorporating this type of correction is an essential step, even in discovery-oriented analysis, to give researchers reasonable guidance on the validity of their discoveries. Due to multi-modalities with varied level of measurement sensitivity/specificity, the traditional level of FDR acceptance (<=5%) may be relaxed and acceptance up to 20% may be considered. Secondary validation on the obtained biomarkers will be used to reduce the false positive & false negative rates.

Unsupervised and Supervised Data Analysis

Depending on the type of analysis, there are both unsupervised and supervised analysis options available. The distinction in these approaches is that unsupervised analysis does not use any outcome variable, but rather provides summary information and/or graphical representations of the data. Supervised analysis, in contrast, creates models that attempt to separate or predict the data with respect to an outcome or phenotype (for instance, patient outcome or response).

Figure 9:
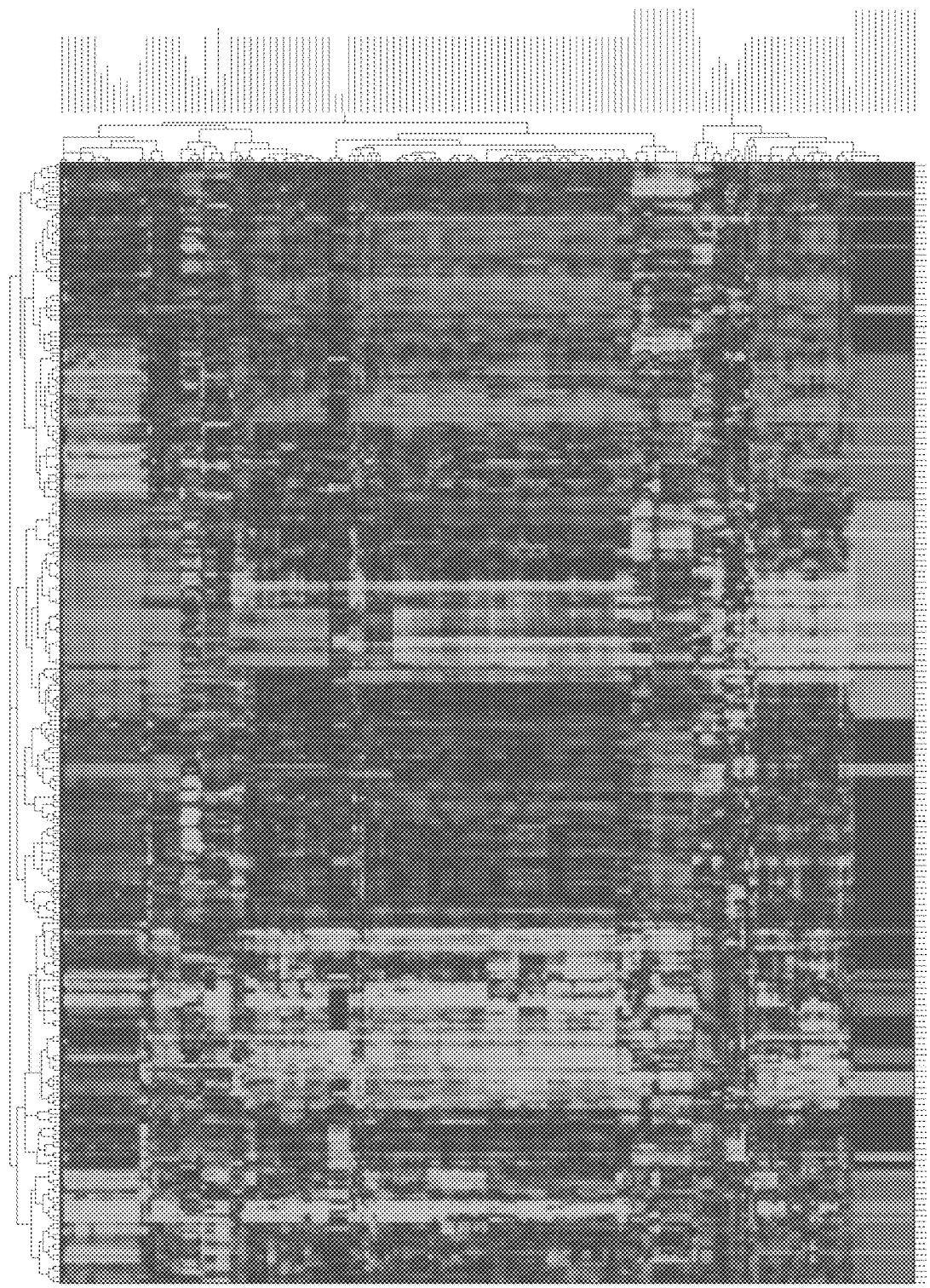
FIG. 9 is a heat map of NSCLC patients with quantitative imaging features extracted.

Clustering is the grouping of like data and is one of the most common unsupervised analysis approaches. There are many different types of clustering, although several general types are commonly used within bioinformatics approaches. Hierarchical clustering, or the assignment of examples into clusters at different levels of similarity into a hierarchy of clusters, is the most common type. Similarity is based on correlation (or Euclidean distance) between individual examples or clusters. Most significantly, the data from this type of analysis can be graphically represented using the cluster heat map. FIG. 9 illustrates a heat map of NSCLC patients with quantitative imaging features extracted. Unsupervised hierarchical clustering of lung tumor image features extracted from CT images from 276 NSCLC patients. Tumor segmentation for each CT image was performed in a semiautomated fashion. Quantitative imaging features were calculated using Definiens (Munchen, Germany) and represent many 2D and 3D characteristics of the tumor. Aspects such as tumor volume, shape and texture were represented. Each of the numerical imaging features was median centered, and all features were clustered using complete linkage, with correlation used as the similarity measure. The resulting heat map is visualized using red to represent higher than median feature values and green to represent lower than median feature values. Each row of the heat map represents a specific imaging feature across patients, and each column represents all features for a patient's lung tumor from CT. The heat map is an intuitive display that simultaneously reveals row and column hierarchical cluster structure in a data matrix that consists of a rectangular tiling with each tile shaded on a color scale to represent the value of the corresponding element of the data matrix. This cluster heat map is a synthesis of various graphic displays developed by statisticians over more than a century. Supervised analysis consists of building a mathematical model of an outcome or response variable. The breadth of techniques available is remarkable and spans statistics and data mining/machine learning. Approaches we have used include neural networks, linear regression and Cox proportional hazards regression.

Some essential criteria in selecting an approach include the stability and reproducibility of the model. Neural networks or ensemble methods, if they involve an element of randomness, can lead to results that cannot be replicated without the same random sequences generated. In light of many of the difficulties surrounding genomic-based models, understandability of the generated models is an important consideration. For clinical validation, alternate assays or measurements may be required, and thus, an understanding of the way in which variables are combined in a decision model is necessary for translation. In the case of NSCLC imaging, methods that generate understandable decisions can be important for combining this information with existing advances in genotyping patients (e.g., EGFR mutation, EML4-ALK rearrangements).

Multivariate data analysis tools such as PCA and partial least squares projection to latent structures (PLS) can be used to analyze quantitative features together with additional data. PCA allows for an unsupervised analysis of the data where important features can be extracted and visualized. PCA extracts the underlying structures, principal components, so that a high-dimensional space can be visualized in a 2D or 3D space. Additional layers of information can be added by using coloring, shapes and size of the objects on the graphs. PCA can be utilized to find grouping, outliers and other artifacts within the data. To find common underlying structures and correlation between two matrices, PLS can be used. PLS has been shown to work well on large and complex data sets with more variables than observations, on collinear variables and where there are some missing data.

A final contribution from the field of bioinformatics is the approach developed to provide validation of prediction findings from high-dimensional experiments. Many genomics-based studies that have been published contain significant analytical errors. These errors compromise the estimates of predictor accuracy or overall findings. Following the best practices in developing and then independently validating the observations in a distinct cohort is essential for reproducible results. For instance, several validation components have been provided, including validation between MAASTRO Clinic (Netherlands) and Moffitt sample sets, as well as validation in prospectively collected Moffitt samples. When model building and cross-validation efforts are completed, the entire group will determine the appropriate model(s) to evaluate in independent validation.

Sample Size Issues

High-throughput technologies (CT images, genomic/proteomic, etc.) provide us with an enormous amount of multivariate data describing the complex biological process. Ability to predict risks or to draw inferences based on clinical outcomes is bogged by sample size. Various cross-validation methods are been studied and unbiased error estimation called the bootstrap have been proposed. Inference in small samples has seen renewed interest with the advent of genomics technologies, especially in classification. There has been extensive studies to make unbiased inference in small samples, one approach was to create synthetic samples following the distribution of the sample groups and report errors of the newly formed population. In addition, most popular error estimates has been studied in context of small sample classification.

Clinical and Risk Factor Data

Incorporating detailed clinical and patient risk factor data into radiomics is important because imaging features may be influenced by patient parameters. Patient parameters may influence the image features via a direct causal association or exert a confounding effect on statistical associations whereby the parameter is correlated with both the independent and dependent variables. For instance, smoking-related lung cancers differ from lung cancers in patients who never smoked, and thus, smoking status could influence image features, clinical parameters (histology), phenotypes, molecular signatures and end points (i.e., survival, recurrence). Addressing the influence of patient parameters in radiomics research by using epidemiologic and biostatistical approaches will minimize spurious relationships by avoiding type I error. Moreover, predictive models which are more precise and clinically relevant may be developed which target well-characterized and -defined patient subgroups rather than a broad heterogeneous disease group. For example, a model that includes all patients with adenocarcinoma of lung would not likely be clinically relevant because of the heterogeneity (biological and clinical) of this histologic subtype. However, a predictive model which focused on adenocarcinoma patients with a specific molecular feature (e.g., EML4-ALK fusion) would likely be informative because of the biological and clinical homogeneity and subsequent targeted therapies. Thus, as noted with the bioinformatics "toolbox," existing epidemiologic and biostatistical approaches can be leveraged towards radiomics research to develop robust and clinically relevant prognostic models, to reveal factors that may influence (casually or by confounding) radiomics features, and to explore and mine complex data sets.

Example Computing Device

Figure 10:
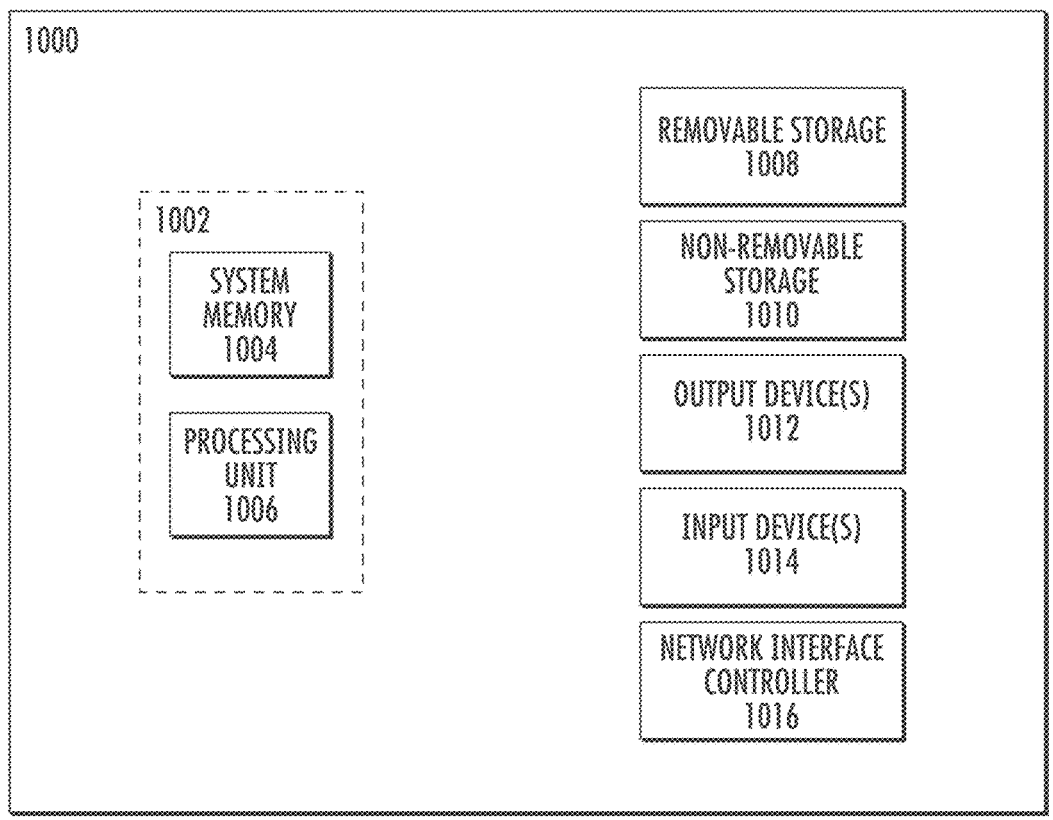
FIG. 10 is a block diagram of an example computing device.

When the logical operations described herein are implemented in software, the process may execute on any type of computing architecture or platform. For example, referring to FIG. 10, an example computing device upon which embodiments of the invention may be implemented is illustrated. The computing device 1000 may include a bus or other communication mechanism for communicating information among various components of the computing device 1000. In its most basic configuration, computing device 1000 typically includes at least one processing unit 1006 and system memory 1004. Depending on the exact configuration and type of computing device, system memory 1004 may be volatile (such as random access memory (RAM)), non-volatile (such as read-only memory (ROM), flash memory, etc.), or some combination of the two. This most basic configuration is illustrated in FIG. 10 by dashed line 1002. The processing unit 1006 may be a standard programmable processor that performs arithmetic and logic operations necessary for operation of the computing device 1000.

Computing device 1000 may have additional features/functionality. For example, computing device 1000 may include additional storage such as removable storage 1008 and non-removable storage 1010 including, but not limited to, magnetic or optical disks or tapes. Computing device 1000 may also contain network connection(s) 1016 that allow the device to communicate with other devices. Computing device 1000 may also have input device(s) 1014 such as a keyboard, mouse, touch screen, etc. Output device(s) 1012 such as a display, speakers, printer, etc. may also be included. The additional devices may be connected to the bus in order to facilitate communication of data among the components of the computing device 1000. All these devices are well known in the art and need not be discussed at length here.

The processing unit 1006 may be configured to execute program code encoded in tangible, computer-readable media. Computer-readable media refers to any media that is capable of providing data that causes the computing device 1000 (i.e., a machine) to operate in a particular fashion.

Various computer-readable media may be utilized to provide instructions to the processing unit 1006 for execution. Common forms of computer-readable media include, for example, magnetic media, optical media, physical media, memory chips or cartridges, a carrier wave, or any other medium from which a computer can read. Example computer-readable media may include, but is not limited to, volatile media, non-volatile media and transmission media. Volatile and non-volatile media may be implemented in any method or technology for storage of information such as computer readable instructions, data structures, program modules or other data and common forms are discussed in detail below. Transmission media may include coaxial cables, copper wires and/or fiber optic cables, as well as acoustic or light waves, such as those generated during radio-wave and infra-red data communication. Example tangible, computer-readable recording media include, but are not limited to, an integrated circuit (e.g., field-programmable gate array or application-specific IC), a hard disk, an optical disk, a magneto-optical disk, a floppy disk, a magnetic tape, a holographic storage medium, a solid-state device, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices.

In an example implementation, the processing unit 1006 may execute program code stored in the system memory 1004. For example, the bus may carry data to the system memory 1004, from which the processing unit 1006 receives and executes instructions. The data received by the system memory 1004 may optionally be stored on the removable storage 1008 or the non-removable storage 1010 before or after execution by the processing unit 1006.

Computing device 1000 typically includes a variety of computer-readable media. Computer-readable media can be any available media that can be accessed by device 1000 and includes both volatile and non-volatile media, removable and non-removable media. Computer storage media include volatile and non-volatile, and removable and non-removable media implemented in any method or technology for storage of information such as computer readable instructions, data structures, program modules or other data. System memory 1004, removable storage 1008, and non-removable storage 1010 are all examples of computer storage media. Computer storage media include, but are not limited to, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by computing device 1000. Any such computer storage media may be part of computing device 1000.

It should be understood that the various techniques described herein may be implemented in connection with hardware or software or, where appropriate, with a combination thereof. Thus, the methods and apparatuses of the presently disclosed subject matter, or certain aspects or portions thereof, may take the form of program code (i.e., instructions) embodied in tangible media, such as floppy diskettes, CD-ROMs, hard drives, or any other machine-readable storage medium wherein, when the program code is loaded into and executed by a machine, such as a computing device, the machine becomes an apparatus for practicing the presently disclosed subject matter. In the case of program code execution on programmable computers, the computing device generally includes a processor, a storage medium readable by the processor (including volatile and non-volatile memory and/or storage elements), at least one input device, and at least one output device. One or more programs may implement or utilize the processes described in connection with the presently disclosed subject matter, e.g., through the use of an application programming interface (API), reusable controls, or the like. Such programs may be implemented in a high level procedural or object-oriented programming language to communicate with a computer system. However, the program(s) can be implemented in assembly or machine language, if desired. In any case, the language may be a compiled or interpreted language and it may be combined with hardware implementations.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed:

1. A method for analyzing quantitative information obtained from radiological images, comprising:
    extracting, by a computing device, one or more quantitative features that describe a region of interest (ROI) or a volume of interest (VOI) in a radiological image;
    storing the one or more quantitative features describing the ROI or the VOI from the radiological image as a radiological image record in a data structure accessible by the computing device, said data structure comprising one or more radiological image records;
    receiving, by the computing device, a request related to a patient's radiological image, the request comprising the patient's radiological image or information related to the patient's radiological image;
    analyzing, by the computing device, the data structure to determine a statistical relationship between the request and the one or more radiological image records; and
    generating, by the computing device, a patient report comprising at least one of a diagnosis, a prognosis or a recommended treatment regimen for the patient's disease based on a result of analyzing the data structure.

2. The method of claim 1, further comprising transmitting, by the computing device, the patient report in response to the request, wherein the patient report further comprises one or more of a probability for at least one of the diagnosis, the prognosis, the recommended treatment regimen for the patient's disease, or a reliability coefficient associated with the probability for at least one of the diagnosis, the prognosis or the recommended treatment regimen for the patient's disease.

3. The method of claim 1, wherein the radiological image record further comprises one or more imaging parameters related to the radiological image and one or more clinical parameters.

4. The method of claim 1, wherein the quantitative features that describe the ROI or the VOI in the radiological image includes one or more of a shape-based feature, a texture-based feature, a habitat feature, an intensity feature or a position-based feature.

5. The method of claim 3, wherein the one or more imaging parameters related to the radiological image comprise at least one of a resolution parameter, a reconstruction parameter and an acquisition parameter and the one or more imaging parameters related to the radiological image are included in a DICOM header of the radiological image.

6. The method of claim 3, wherein the clinical parameters comprise at least one of a disease type, a disease stage, a treatment history or a clinical outcome.

7. The method of claim 6, wherein the treatment history comprises a treatment regimen, wherein the treatment regimen is at least one of a prescribed drug, a clinical trial or a medical procedure or wherein the treatment history further comprises information about the prescribed drug including at least one of a name, a strength or a number of refills of the prescribed drug or wherein the treatment history further comprises information about a change in a disease and a treatment regimen prescribed in response to the change in the disease, wherein the change in the disease is a relapse of the disease or a healing of the disease.

8. The method of claim 6, wherein the clinical outcome comprises at least one of a response to therapy, a time to progression, a progression-free survival, a disease-free survival or an overall survival, or wherein the clinical outcome comprises at least one of an objective assessment of response to therapy or a subjective assessment of response to therapy.

9. The method of claim 1, wherein the radiological image record further comprises one or more of molecular, genetic, genomic, proteomic data, or demographic data.

10. The method of claim 1, wherein analyzing, by the computing device, the data structure to determine a statistical relationship between the request and the one or more radiological image records comprises the computing device using a pattern recognition technique to identify patterns relevant to the patient's disease that are present in the data structure.

11. The method of claim 10, wherein the pattern recognition technique is a distance matching algorithm.

12. The method of claim 1, wherein the request related to the patient's radiological image comprises the patient' radiological image, the method further comprising:
  identifying, by the computing device, a ROI or a VOI in the patient's radiological image;
  segmenting the ROI or the VOI from the patient's radiological image; and
  extracting, by the computing device, one or more quantitative features that describe the ROI or the VOI from the patient's radiological image, wherein the information related to the patient's radiological image comprises the one or more quantitative features that describe the ROI or the VOI from the patient's radiological image and one or more imaging parameters related to the patient's radiological image.

13. The method of claim 1, wherein the request related to the patient's radiological image comprises the information related to the patient's radiological image, and wherein the information related to the patient's radiological image comprises one or more of a plurality of quantitative features that describe a ROI or a VOI in the patient's radiological image and one or more imaging parameters related to the patient's radiological image, or the patient's molecular, genetic, genomic or proteomic, tissue data or the patient's demographic data.

14. The method of claim 1, wherein extracting, by the computing device, the one or more quantitative features that describe the ROI or the VOI in the radiological image further comprises extracting one or more quantitative features that describe an area at least partially surrounding the ROI or the VOI in the radiological image.

15. The method of claim 1, wherein the ROI or the VOI in the radiological image is segmented from the radiological image by the computing device using at least one of a region-growing algorithm, a level set algorithm, a graph cut algorithm, an active contour algorithm and a livewire algorithm.

16. The method of claim 1, further comprising:
  stripping, by the computing device, confidential patient information from the radiological image; and
  assigning, by the computing device, the radiological image a de-identified number, wherein the radiological image record further comprises the de-identified number.

17. The method of claim 1, wherein the radiological image is obtained by at least one of computed tomography (CT), magnetic resonance imaging (MRI) or positron emission tomography (PET).

18. A method for analyzing quantitative information obtained from radiological images, comprising:
  extracting, by a computing device, one or more quantitative features that describe a region of interest (ROI) or a volume of interest (VOI) from a patient's radiological image;
  transmitting, by the computing device, a request comprising the one or more quantitative features that describe the ROI or the VOI from the patient's radiological image; and
  receiving, by the computing device, a patient report in response to the request, the patient report comprising at least one of a diagnosis, a prognosis or a recommended treatment regimen for the patient's disease,
  wherein the patient report is obtained by analyzing a data structure comprising one or more radiological image records to determine a statistical relationship between the request and the one or more radiological image records, and wherein each of the one or more radiological image records stored in the data structure comprises a plurality of quantitative features that describe a ROI or a VOI in each respective radiological image.

19. The method of claim 18, wherein the request further comprises one or more imaging parameters related to the patient's radiological image.

20. The method of claim 19, wherein the one or more imaging parameters related to the patient's radiological image comprise at least one of a resolution parameter, a reconstruction parameter and an acquisition parameter, and wherein the one or more imaging parameters related to the patient's radiological image are included in a DICOM header of the patient's radiological image.

21. The method of claim 18, wherein each of the one or more radiological image records stored in the data structure further comprises one or more imaging parameters related to each respective radiological image and one or more clinical parameters.

22. The method of claim 18, wherein the request further comprises the patient's molecular, genetic, genomic or proteomic data, tissue data or the patient's demographic data.

23. The method of claim 18, wherein the quantitative features that describe the ROI or the VOI in the patient's radiological image include one or more of a shape-based feature, a texture-based feature a habitat feature, an intensity feature or a position-based feature.

24. The method of claim 18, wherein extracting, by the computing device, the one or more quantitative features that describe the ROI or the VOI in the patient's radiological image further comprises extracting one or more quantitative features that describe an area at least partially surrounding the ROI or the VOI in the patient's radiological image, wherein the ROI or the VOI in the radiological image is segmented from the radiological image using at least one of a region-growing algorithm, a level set algorithm, a graph cut algorithm, an active contour algorithm and a livewire algorithm.

* * * * *